(12) United States Patent
Virshup et al.

(10) Patent No.: US 10,092,251 B2
(45) Date of Patent: Oct. 9, 2018

(54) PROSPECTIVE EVALUATION OF TUMOR VISIBILITY FOR IGRT USING TEMPLATES GENERATED FROM PLANNING CT AND CONTOURS

(71) Applicant: Varian Medical Systems, Inc., Palo Alto, CA (US)

(72) Inventors: Gary Fredric Virshup, Cupertino, CA (US); Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 521 days.

(21) Appl. No.: 14/206,415

(22) Filed: Mar. 12, 2014

(65) Prior Publication Data

US 2014/0275705 A1   Sep. 18, 2014

Related U.S. Application Data

(60) Provisional application No. 61/799,195, filed on Mar. 15, 2013.

(51) Int. Cl.
*A61N 5/10* (2006.01)
*A61B 6/03* (2006.01)
(Continued)

(52) U.S. Cl.
CPC ............. *A61B 6/032* (2013.01); *A61N 5/103* (2013.01); *A61N 5/1037* (2013.01); *A61B 6/025* (2013.01); *A61B 6/482* (2013.01)

(58) Field of Classification Search
CPC ........ A61N 5/10; A61N 5/103; A61N 5/1031; A61N 5/1037; A61N 5/1039;
(Continued)

(56) References Cited

U.S. PATENT DOCUMENTS 6,307,914 B1   10/2001   Kunieda et al.
6,888,919 B2    5/2005   Graf
(Continued)

FOREIGN PATENT DOCUMENTS

JP   2004-041725 A   2/2004

OTHER PUBLICATIONS

Mostafavi et al., "Detection and Localization of Radiotheraphy Targets by Template Matching" 34th Annual International Conference of the IEEE Engineering in Medicine and Biology Society, pp. 6023-6027, Aug./Sep. 2012.
(Continued)

*Primary Examiner* — Thaddeus Cox
(74) *Attorney, Agent, or Firm* — Vista IP Law Group, LLP

(57) ABSTRACT

The plan CT is described to generate dual energy (DRR) that stimulates the treatment time radiographs in order to prospectively evaluate the angles in which issues for the template matching algorithm are present, and thus the visibility of the tumor. The present invention uses template matching to quantify the "trackability" of the target from different angles or directions. The peak-to-side lobe ratio is used to measure trackability. The results of this process influence treatment planning. For example, based on the outcome, either less or no dose is planned for the angles in which the location of the templates cannot be verified and thus, the tumor.

23 Claims, 19 Drawing Sheets

(51) Int. Cl.
    *A61B 6/02*           (2006.01)
    *A61B 6/00*           (2006.01)

(58) Field of Classification Search
    CPC ........ A61N 5/1048; A61B 6/032; A61B 6/40; A61B 6/025; A61B 6/4021; A61B 6/4028; A61B 6/42; A61B 6/52; A61B 6/5205; A61B 6/5211; A61B 6/5258
    See application file for complete search history.

(56) References Cited

U.S. PATENT DOCUMENTS

| | | | |
|---|---|---|---|
| 6,937,696 | B1 | 8/2005 | Mostafavi |
| 7,649,981 | B2 | 1/2010 | Seppi et al. |
| 2007/0078306 | A1 | 4/2007 | Allison et al. |
| 2007/0291895 | A1* | 12/2007 | Yin ................. A61B 6/025 378/20 |
| 2008/0240353 | A1 | 10/2008 | Myles |
| 2009/0279761 | A1* | 11/2009 | Fei ................... A61B 6/12 382/130 |
| 2010/0080354 | A1 | 4/2010 | Fu et al. |
| 2012/0008735 | A1 | 1/2012 | Maurer et al. |
| 2012/0027162 | A1 | 2/2012 | Garnica Garza |
| 2014/0119623 | A1 | 5/2014 | Mostafavi et al. |

OTHER PUBLICATIONS

De Man et al., "Distance-driven Projection and Backprojection in Three Dimensions," Institute of Physics Publishing, pp. 2463-2475, May 19, 2004.

Long et al., "3D Forward and Back-Projection of X-Ray CT Using Separable Footprints," IEEE Transactions on Medical Imaging, vol. 29, No. 11, pp. 1839-1850, Nov. 2010.

Robert L. Siddon, "Fast Calculation of the Exact Radiological Path for a Three-Dimensional CT Array," Medical Physics, vol. 12, No. 2, pp. 252-255, Mar./Apr. 1985.

International Search Report and Written Opinion dated Jul. 30, 2014 for related PCT Patent Application No. PCT/US2014/028893, 14 pages.

De Man, Bruno et al., "Distance-driven Projection and Backprojection in Three Dimensions," Institute of Physics Publishing, Phys. Med. Biol. 49 (2004); pp. 2463-2475.

Long, Yong et al., "3D Forward and Back-Projection for X-Ray CT Using Separable Footprints," IEEE Transactions on Medical Imaging, vol. 29, No. 1 (Nov. 2010); pp. 1839-1850.

Siddon, Robert L., "Fast Calculation of the Exact Radiological Path for a Three-Dimensional CT Array," Department of Radiation Therapy and Joint Center for Radiation Therapy, vol. 12, No. 2 (1985); pp. 252-255.

Mostafavi, Hassan et al. "Deterction and Localization of Radiotherapy Targets by Template Matching,"; 5 pages.

U.S. Appl. No. 13/662,365, entitled "Template Matching Method for Image-Based Detection and Tracking of Irregular Shaped Targets," filed Oct. 26, 2012.

Extended European Search Report dated Oct. 10, 2016 for corresponding EP Patent Application No. 14763593.2, 9 pages.

Mostafavi H et al., "Detection and locatlization of radiotherapy targets by template matching", The Effect of Applied Compressive Loading on Tissue-Engineered Cartilage Constructs Cultured with TGF-BETA3-, IEEE, Aug. 28, 2012, 5 pages.

Chinese Office Action dated Sep. 1, 2017 for corresponding CN Patent Application No. 2014800262924, 15 pages.

Chinese Office Action dated Feb. 27, 2018 for corresponding CN Patent Application No. 2014800262924, 12 pages.

* cited by examiner

Generating Template Method
186

188
Receiving an input from a user representing an identification of the object by the user.

190
Using the input to determine a volume of interest (VOI) that includes voxels of a volumetric image.

192
Determine a template using at least some of the voxels in the VOI.

FIG. 10

PROSPECTIVE EVALUATION OF TUMOR VISIBILITY FOR IGRT USING TEMPLATES GENERATED FROM PLANNING CT AND CONTOURS

CROSS REFERENCE TO RELATED APPLICATIONS

This application claims priority to U.S. Provisional Application Ser. No. 61/799,195 entitled "Prospective Evaluation of Tumor Visibility for IGRT Using Templates Generated from Planning CT and Contours," filed on 15 Mar. 2013, the disclosure of which is incorporated herein by reference in its entirety. Commonly owned U.S. patent application Ser. No. 13/662,365, filed Oct. 26, 2012, the disclosure of which is incorporated by reference herein in its entirety.

BACKGROUND

Field of the Invention

This application relates generally to medical imaging and, more particularly, to the systems and methods for evaluation of tumor visibility in images, both markerless and with implanted markers.

Related Art

Radiotherapy has been used in the treatment of tumors, such as tumors in the lungs and abdomen. Localizing the tumors during treatment time allows more precise dose delivery, which is crucial to maximize the ratio between tumor dose and normal tissue dose. Since these tumors may move during treatment, the ability to track the tumors is important and is critical for image guided radiotherapy (IGRT). Tracking the tumor can be done with multiple modalities, including implanted markers, implanted beacons as well. As some therapists are hesitant to implant markers into patients, there is markerless tracking technology. Markerless tumor tracking technologies can use derived tumor location templates to match with x-ray generated images. Sometimes these x-ray generated images may be simple radiographs, but sometimes better tracking may be accomplished with other imaging modalities such as Dual kV Radiographs, which can remove interfering bone structures, or Digital Tomosynthesis images.

SUMMARY OF THE INVENTION

Embodiments of the present disclosure are directed to methods, computer systems, and computer program products to a planning computed tomography (CT) with an image-based localization optimizer engine for generating single energy (SE) digital reconstructed radiographs (DRR) or dual energy (DE) DRR that simulates the treatment time radiographs in order to prospectively evaluate the angles in which issues for the template matching algorithm are present, and thus the visibility of the tumor, prior to treatment. The image-based localization optimizer engine is configured to generalize for optimizing the templates, modalities, and angles prior to treatment to enable making a more informed choice on modality during treatment.

The image-based localization optimizer engine comprises an input module for receiving angles, planning images, planning data, templates, modalities, a template generator module, a digital reconstructed image (DRI) generator module, an optimization/search module, a template matching module, and an output module for generating a matrix of trackability as a function of an angle, template types, and image modality.

The image-based localization optimizer engine is configured to use template matching to quantify the trackability of the target from different angles or directions. The peak-to-side lobe ratio is used to measure trackability. The results of this process influence treatment planning. For example, based on the outcome, either less or no dose is planned for the angles in which the location of the templates cannot be verified and thus, the tumor.

The image-based localization optimizer engine is configured to use a planning CT in order to prospectively quantify tumor visibility for the purpose of automatic its localization at treatment time. The plan CT's systems and methods prospectively generate a template for each angle from which the tumor is to be imaged during treatment. These online imaging angles are also used to simulate online images. These can be SE DRR, DE DRR, digital tomosynthesis (DTS), or megavoltage (MV) images, which simulate treatment time images obtainable from different angles during the treatment. The template matching of these simulated online images and corresponding templates is used to quantify tumor visibility for that angle, template type, and online imaging modality. One method for quantifying is based on analyzing the match score surface output of template matching and calculating the peak-to-sidelobe ratio (PSR).

The image-based localization optimizer engine is configured to provide a prediction that is used in treatment planning or in targeting a dose or treatment at an angle where the tumor is predicted to be; in other words, placing a dosage in an area where there is high confidence that a tumor is located and thus, is being tracked. With a plan CT, doctors contour the tumor, the bones, and other the organs at risk. This invention uses the idea of dual energy DRRs as an effective source to evaluate whether or not dual energy gives you a better image for tumor tracking treatment. The invention uses a template technique to match the way in which a tumor may be evaluated during the use of a treatment. Additionally, the invention is used to determine whether a single energy digital reconstructive radiograph or a dual energy digital reconstructive radiograph gives you better results.

Prospective and quantitative assessment of tumor visibility in online images for IGRT has not been proposed before nor has the use of planning CT and contouring as an effective implementation of a method for achieving this goal. Using the results of this method for optimizing a treatment plan and IGRT process is novel.

Template matching has been developed to locate moving objects. For radiotherapy patients, the doctors develop a plan. While developing the plan, doctors contour numerous objects in the 3-d plan CT. The template matching algorithm takes a subset of these contours, as well as the CT voxels enclosed by them, and develop a template which is then matched to a treatment time radiographic image for the monitoring the position of the tumor during dose delivery.

This method is particularly effective in the treatment of tumors without implanting a localizing fiducial, such as a radio-opaque marker or an RF beacon. The method is also effective when implanted radio-opaque markers assume irregular shapes in the body after implantation. The matching is done at different offsets of the template relative to the online image, in order to account for possible motion of the target within an allowable margin.

The value of the match score at different offsets is viewed as a "match score surface." The ability of the algorithm to work depends upon the ratio of the peak match score, corresponding to the target position, to side lobes of the match score surface. A higher ratio means more confidence in having correctly located the target in the radiographic image.

As the contours are three-dimensional structures in the plan CT, the structures can be used to develop templates for all angles of treatment, either coplanar or non-coplanar.

Broadly stated, a method to optimize tracking of radiotherapy targets as part of treatment planning, comprising simulating by a computer a treatment time image by from treatment planning images and data; generating by computer a template from the planning images and data; template matching by a computer between the template and simulated image to quantify the trackability of tumors as part of treatment planning; and optimizing by computer the selection of a template generation and imaging modality for each imaging angle during the treatment to maximize a trackability measure.

The structures and methods of the present invention are disclosed in the detailed description below. This summary does not purport to define the invention. The invention is defined by the claims. These and other embodiments, features, aspects, and advantages of the invention will become better understood with regard to the following description, appended claims, and accompanying drawings.

BRIEF DESCRIPTION OF THE DRAWINGS

The invention will be described with respect to specific embodiments thereof, and reference will be made to the drawings, in which:

FIG. 10 is a block diagram illustrating a method of generating a template in accordance with some embodiments of the present invention.

DETAILED DESCRIPTION

Figure 1:
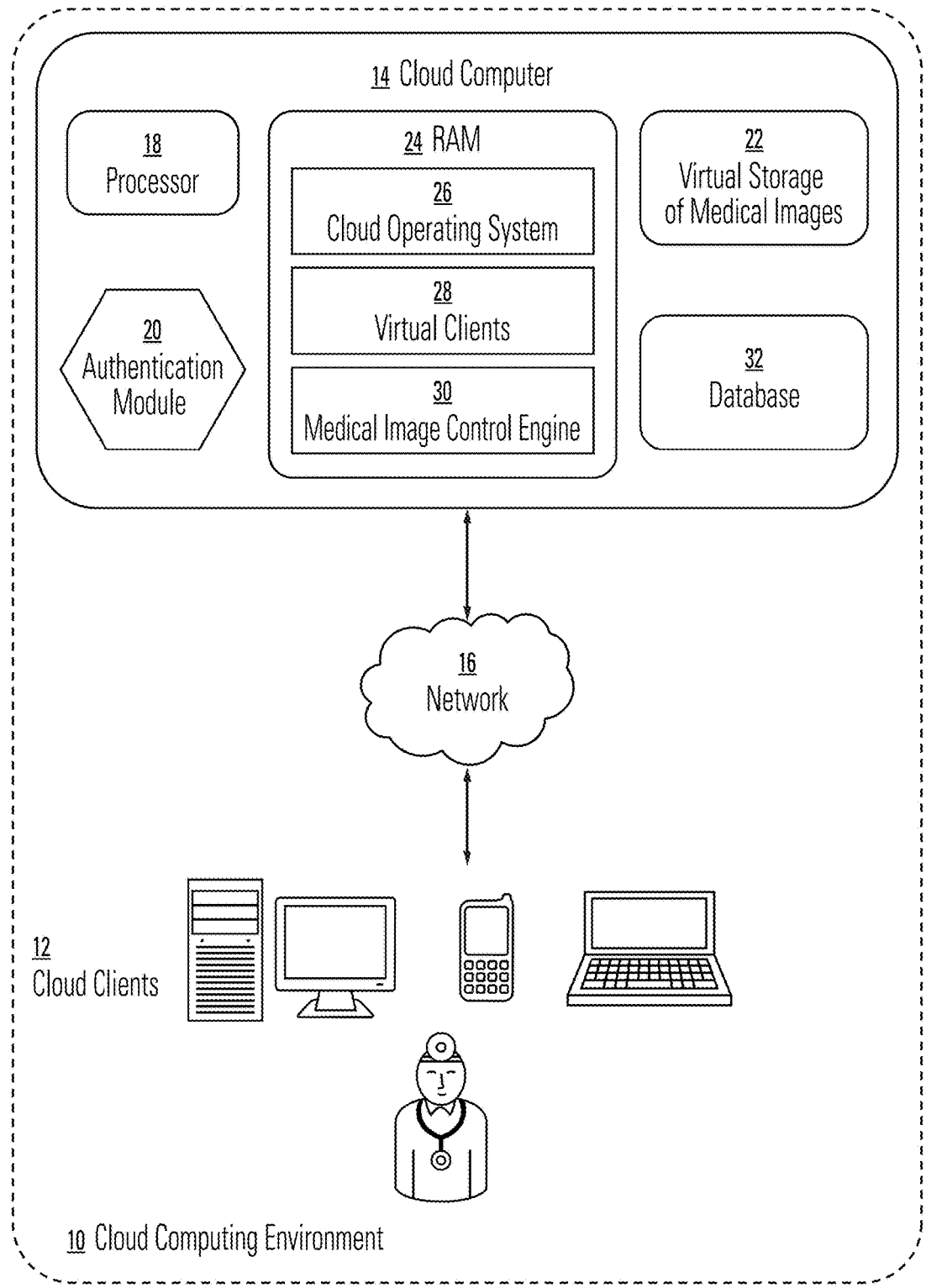
FIG. 1 is a high-level block diagram illustrating a cloud computer in a cloud computing environment in accordance with the present invention.

A description of structural embodiments and methods of the present invention is provided with reference to FIGS. 1-17. It is to be understood that there is no intention to limit the invention to the specifically disclosed embodiments but that the invention may be practiced using other features, elements, methods, and embodiments. Like elements in various embodiments are commonly referred to with like reference numerals.

FIG. 1 is a high-level block diagram illustrating a system embodiment of a cloud computing environment 10 in accordance with the present invention accessible by cloud clients 12 for a physician to view and adjust window/level parameters of multiple image displays. A cloud computer 14 running a cloud operating system, which may include other additional cloud computers, for data communications. The cloud clients 12 communicate with the cloud computer 14 through the network 16, either wirelessly or via a wired connection. The cloud clients 12 are broadly defined to include, but not limited to, desktop computers, mobile devices, notebook computers, SmartTVs, and SmartAutos. A variety of mobile devices are applicable to the present invention including mobile phones, smartphones like iPhones, tablet computers like iPads, and browser-based notebook computers like Chromebooks, with a processor, a memory, a screen, with connection capabilities of Wireless Local Area Network (WLAN), and Wide Area Network (WAN). The mobile device is configured with a full or partial operating system (OS) software, which provides a platform for running basic and advanced software applications. The mobile device functioning as the cloud clients 12 access the cloud computer 14 through a web browser.

In this embodiment, the cloud computer 14 (also referred to as a web/HTTP server) comprises a processor 18, an authentication module 20, a virtual storage of medical images 22, a RAM 24 for executing a cloud operating system 26, virtual clients 28, a medical image control engine 30, and a database 32. The database 32 can be incorporated as part of the cloud computer 14 or external to the cloud computer 14 by being communicatively coupled to the network 16. The cloud computer 14 can be implemented as a module of automated computing machinery installed and operating on one of the cloud computers. In some embodiments, the cloud computer's 14 operating system can include several submodules for providing its intended functional features, such as the virtual clients 28, the medical image control engine 30, and the virtual storage of medical images 22.

In an alternate embodiment, the authentication module 20 can be implemented as an authentication server. The authentication module 20 is configured to authenticate, and grant permission, whether the cloud client 12 is an authorized user to access one or more medical images associated with a particular patient in the virtual storage 22. The authentication server 20 may employ a variety of authentication protocols to authenticate the user, such as a Transport Layer Security (TLS) or Secure Socket Layer (SSL), which are cryptographic protocols that provide security for communications over networks like the Internet.

Medical images can be stored in the virtual storage 22 of the cloud computer 14 in the cloud computing environment 10. The cloud client 12, such as a smartphone or a tablet computer, is capable of accessing the virtual storage of medical images 22 in the cloud computer 14 through the network 16 and displays medical images on the display of the cloud client 12. A physician would be able to view and adjust the medical images from a remote location on a handheld device.

Figure 2:
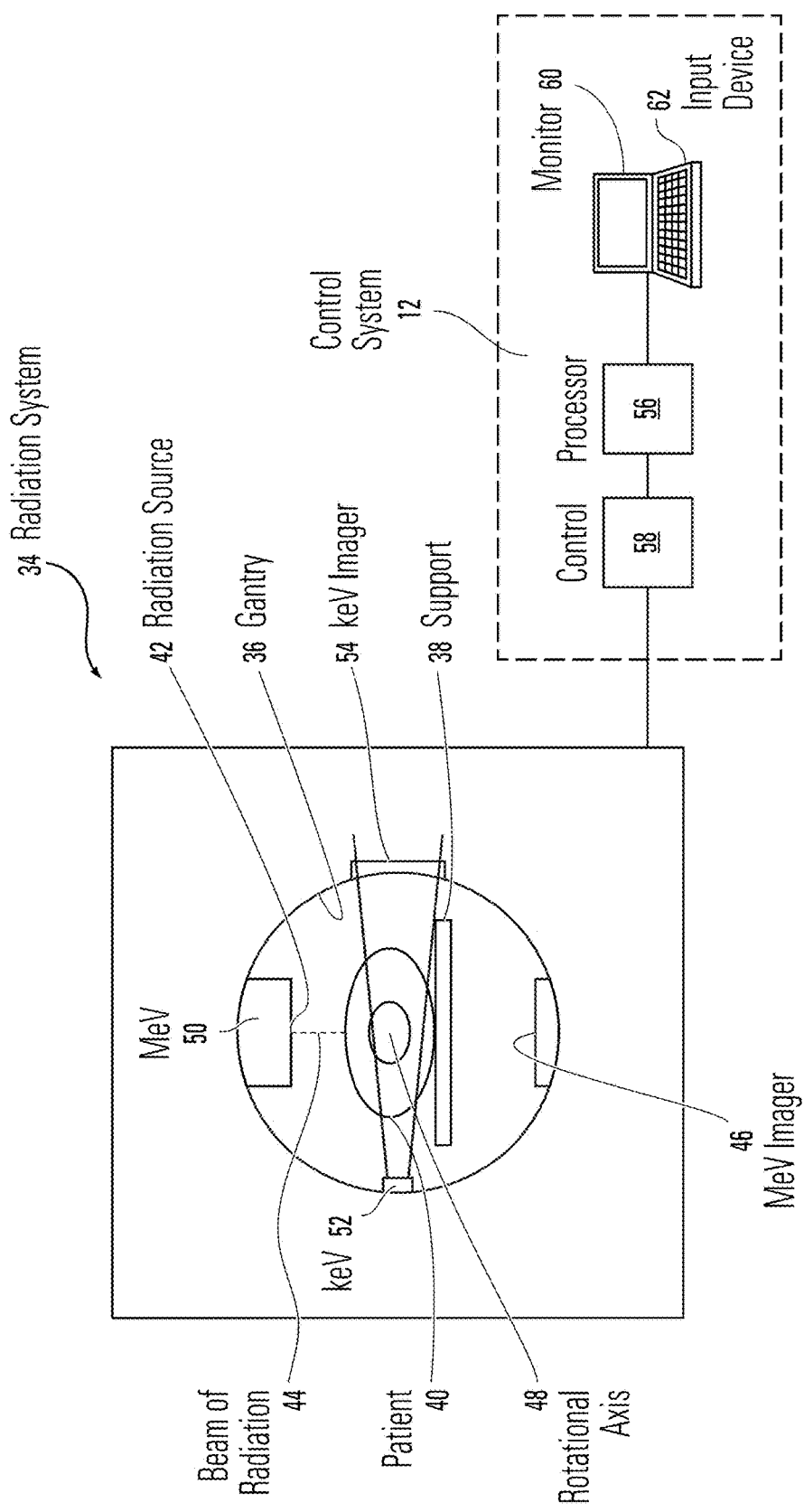
FIG. 2 is a diagram illustrating a radiation system that is used to implement one or more embodiments in accordance with the present invention.

FIG. 2 illustrates a radiation system 34 that may be used to implement one or more embodiments described herein. The system 34 includes a gantry 36, a patient support 38 for supporting a patient 40, and a control system 12 (or 14) for controlling an operation of the gantry 36. The system 34 also includes a therapeutic radiation source 42 that projects a beam 44 of radiation towards the patient 40 while the patient 40 is supported on support 38, and an imager 46, as well as a rotational axis 48, located at an operative position relative to the radiation source 42 (e.g., under the support 14). The radiation source 42 can be configured to generate a cone beam, a fan beam, or other types of radiation beams in different embodiments.

In the illustrated embodiments, the radiation source 42 is a diagnostic radiation source for providing diagnostic energy. In such cases, the imager 46 is configured to receive diagnostic radiation and generate image signals in response thereto. In other embodiments, in addition to being a diagnostic radiation source, the radiation source 42 is also a treatment radiation source for providing treatment energy. In such cases, the imager 46 is configured to selectively receive diagnostic radiation or treatment radiation and generate image signals in response thereto. In further embodiments, instead of being a diagnostic radiation source, the radiation source 42 is a treatment radiation source. In such cases, the imager 46 is configured to receive treatment radiation and generate image signals in response thereto. In the embodiments in which the radiation source 46 is configured to deliver treatment radiation, the system 34 may optionally further include a collimator for changing a characteristic (e.g., shape) of the radiation beam.

In some embodiments, the treatment energy is generally those energies of 160 kilo-electron-volts (keV) or greater, and more typically 1 megaelectron-volts (MeV) or greater, and diagnostic energy is generally those energies below the high energy range, and more typically below 160 keV. For example in one embodiment, which is intended to provide an illustration and does not limit the present disclosure, treatment energies in the range of megaelectron-volts are applied to a location 50, treatment energies in the range of kilo-electron-volts are applied to a location 52, and treatment energies in the range of kilo-electron-volts are applied to a location 54. In other embodiments, the treatment energy and the diagnostic energy can have other energy levels, and refer to energies that are used for treatment and diagnostic purposes, respectively. In some embodiments, the radiation source 42 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and in U.S. patent application Ser. No. 10/687,573, entitled "MULTI-ENERGY XRAY SOURCE," filed on Oct. 15, 2003. In the illustrated embodiments, the radiation source 42 is coupled to a ring gantry and is located within a bore. In other embodiments, the radiation source 42 may be coupled to an arm gantry.

In the illustrated embodiments, the control system 12 includes a processor 56, such as a computer processor, coupled to a control 58. The control system 12 may also include a monitor 60 for displaying data and an input device 62, such as a keyboard or a mouse, for inputting data. In the illustrated embodiments, the gantry 36 is rotatable about the patient 40 and during an imaging and/or a treatment procedure, the gantry 36 rotates about the patient 40 (as in a CT procedure and/or an arch-therapy). In other embodiments, the gantry 36 does not rotate about the patient 40 during a procedure. In such case, the gantry 36 may be fixed, and the patient support 38 is rotatable. The operation of the radiation source 42 and the gantry 36 (if the gantry 36 is rotatable) are controlled by the control 58, which provides power and timing signals to the radiation source 42 and controls a rotational speed and position of the gantry 36, based on signals received from the processor 56. Although the control 58 is shown as a separate component from the gantry 36 and the processor 56, in alternative embodiments, the control 58 can be incorporated as part of the gantry 36 or the processor 56.

It should be noted that the radiation system 34 is not limited to the example described above and that the radiation system 34 may have other configurations in other embodiments. For example, in other embodiments, the radiation system 34 may have different shapes. In other embodiments, the radiation system 34 may have different ranges of motions and/or degrees of freedom. For example, in other embodiments, the radiation source 42 may be rotatable about the patient 40 completely through a 360° range, or partially through a range, that is less than 360°. In addition, in other embodiments, the radiation source 42 is translatable relative to the patient 40. In still further embodiments, the radiation system 34 may be any imaging system that has imaging capability.

Figure 3:
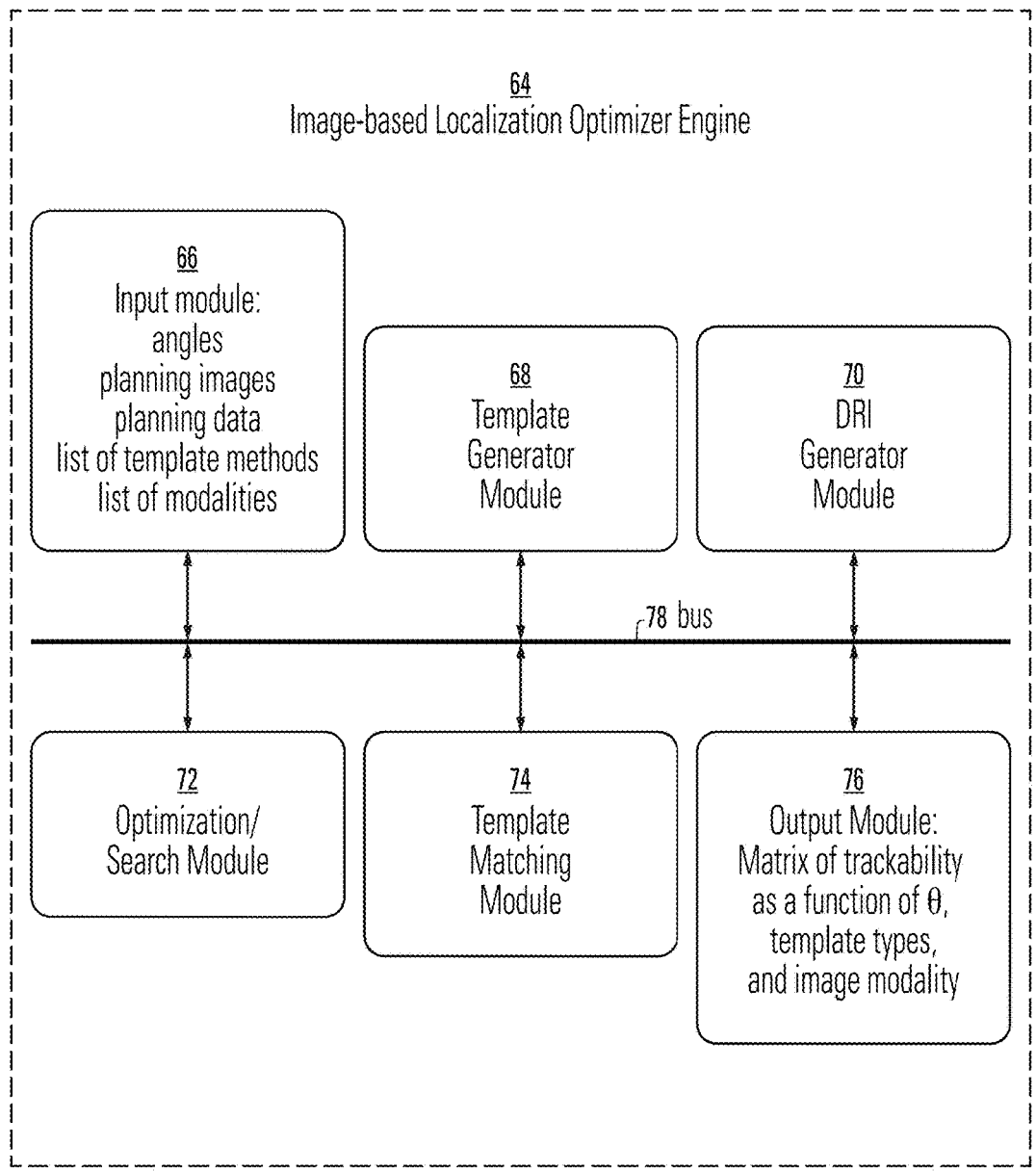
FIG. 3 is a software system diagram illustrating an image-based localization optimizer engine in accordance with the present invention.

FIG. 3 is a software system diagram illustrating an image-based localization optimizer engine 64, which can be software that is installed in the cloud client 12, cloud computer 14 or any computing device. The image-based localization optimizer engine 64 includes an input module 66, a template generator 68, a digital reconstructed image (DRI) generator module 70, an optimization/search module 72, a template matching module 74 and an output module 76. The input module 66 is configured to receive a plurality of inputs, such as angles θ, planning images, planning data, a list of template methods and a list of modalities. The template generator 68 is configured to generate various types of templates from a stored memory. The DRI generator module 70 is configured to digitally reconstruct images. The optimization/search module 72 is configured to execute the process in assessing the angles θ, the types of templates, and the different modalities for optimizing the selection of a template. The template matching module 74 is configured within a search region to compare a template with one of the modalities, such as SE DRR, and DE DRR. For additional information on SE DRR and DE DRR, see Mostafavi et al., "Detection and Localization of Radiotherapy Targets by Template Matching," 34th Annual International Conference of the IEEE Engineering in Medicine and Biology Society, pp. 6023-6027, August/September 2012; De Man et al., "Distance-driven Projection and Backprojection in Three Dimensions," Institute of Physics Publishing, pp. 2463-2475, 19 May 2004; Long et al., "3D Forward and Back-Projection of X-Ray CT Using Separable Footprints," IEEE Transactions on Medical Imaging, Vol. 29, No. 11, pp. 1839-1850, November 2010; Robert L. Siddon, "Fast Calculation of the Exact Radiological Path for a Three-Dimensional CT Array," Medical Physics, Vol. 12, No. 2, pp. 252-255, March/April 1985, which are all incorporated by reference herein in their entireties. The output module 76 is configured to generate a matrix of trackability as a function of θ, template types and image modality.

Figure 4A:
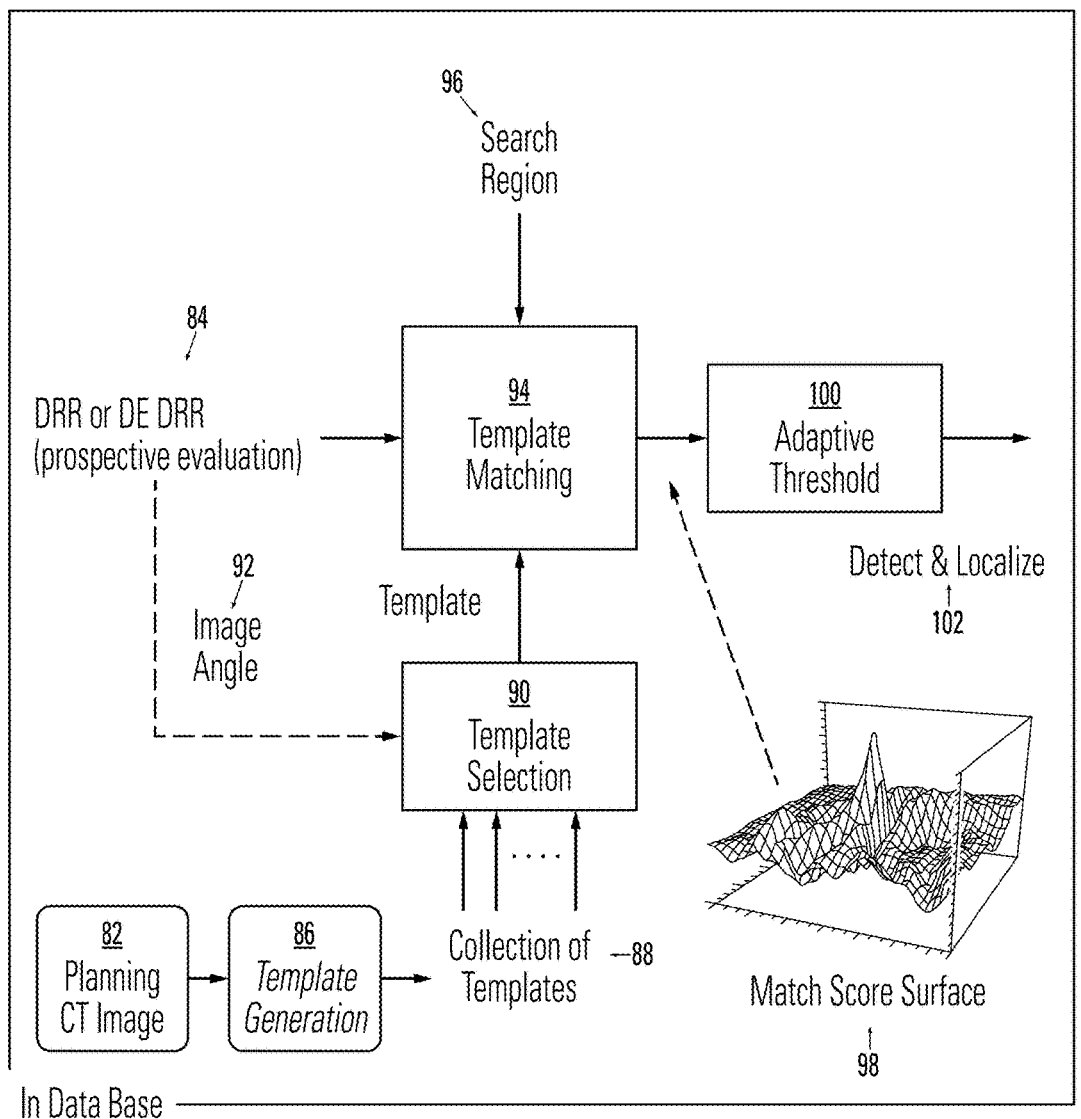
FIG. 4A is a block diagram illustrating a template matching algorithm for prospective evaluation in accordance with the present invention.
Figure 4B:
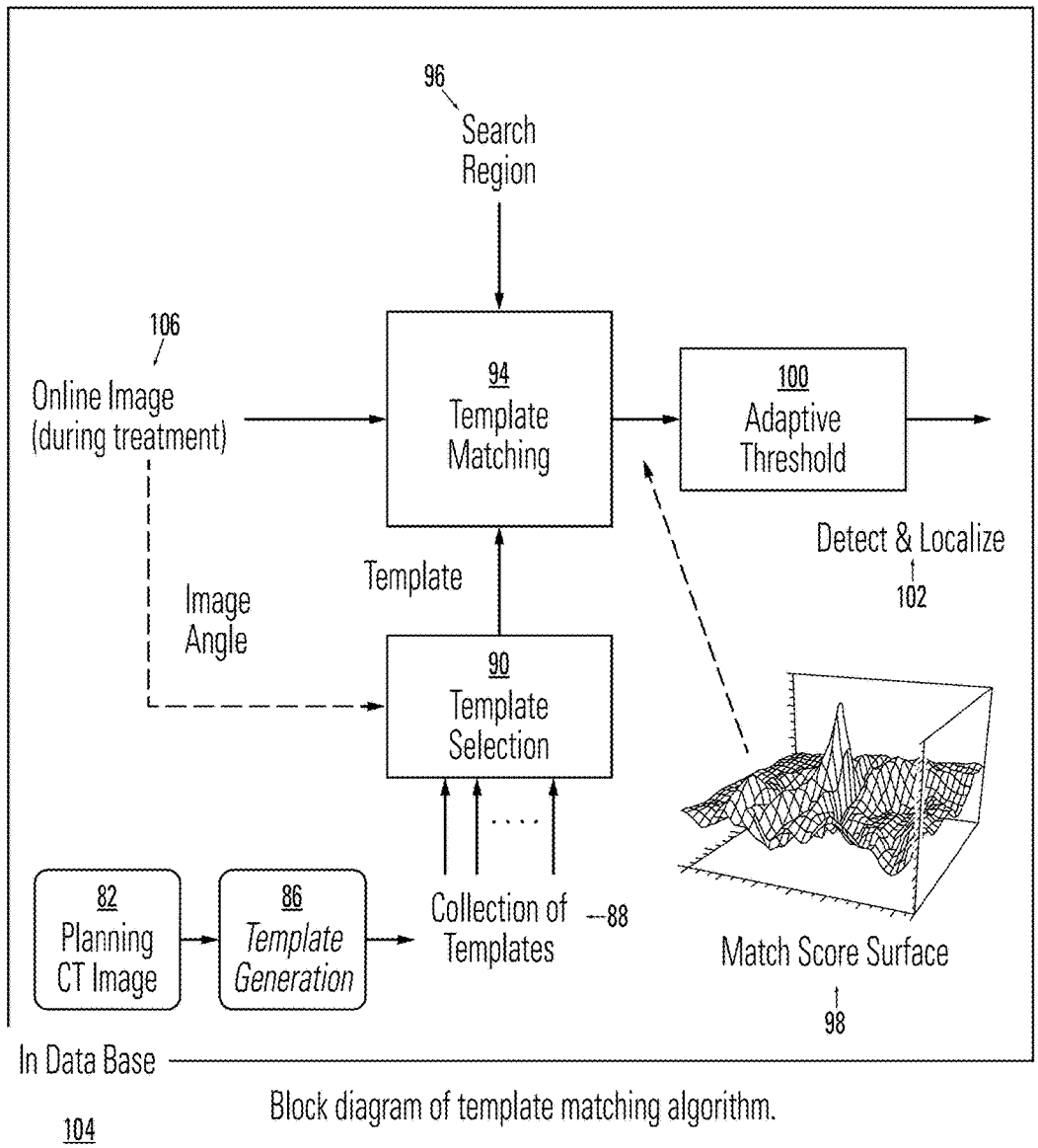
FIG. 4B is a block diagram illustrating a template matching algorithm during treatment in accordance with the present invention.

FIG. 4A is a block diagram illustrating a template matching algorithm 80 for prospective evaluation with DRR or DE DRR 84, while FIG. 4B is a block diagram illustrating a template matching algorithm 104 during treatment with an online image 106. The template algorithms 80 and 104 are directed for template generation and template matching, followed by analysis of the match score surface for detection and localization of the target. Embodiments of the present disclosure are directed to template generation for both markerless tumors and tumors with implanted markers. Differences between template generation for markerless tumors and template generation with implanted markers or fiducials are minimal because both use contours drawn during treatment planning.

At step 82, the image-based localization optimizer engine 64 is configured for planning CT image. To generate the template from a CT image for a given X-ray source rotation angle, at step 86, the template generator module 68 is configured to specify a volume of interest (VOI) around the set of fiducials. Then the template is generated by forward projection of the voxels inside the VOI, using the imaging geometry corresponding to the simulated source angle. Multiple fiducials implanted close to each other can be grouped to form a collection (or a single set) of templates at step 88. In order to demonstrate the ability to track from all gantry angles, the image-based localization optimizer engine 64 is configured to generate CT-based templates for M plurality of simulated gantry angles (e.g., M=120) spaced at N degrees (e.g. N=3) at step 92, thus covering the 360-degree full rotation, and for subsequent template selection at step 90. At step 102, detection and localization of a target is performed by calculating a measure of similarity, called the match score at step 98 and proceeds through an adaptive threshold at step 100, between the template and the DRR or DE DRR 84 in FIG. 4A or between the template and the online projection image in FIG. 4B, at different offsets over a search region of interest (ROI). At step 96, the search ROI is centered at the expected target position and its dimensions are defined by the motion margin expected in each direction. At step 94, the image-based localization optimizer engine 64 is configured to compute template matching, drawing from three input sources, DRR or DE DRR 84, the template selection 90, and the search region 96. The choice of a particular similarity measure as a match score depends on imaging modality and expected differences between the template and the DRR or DE DRR in FIG. 4A, or between the template and the online image in FIG. 4B. Normalized cross correlation and mutual information are two possible methods to generate a match score. Mutual information performs well when geometric patterns are consistent between the images but there are random contrast differences, including contrast reversals. This can occur mostly when the template and the online image correspond to different modalities, e.g., when matching PET or MRI to CT images. A normalized cross correlation is used, which is computationally faster than mutual information, to compute the match score since in data both the template and the online image are generated by X-rays. Calculating the match score at different pixel offsets produces the match score surface defined over the search region, an example of which is shown in FIGS. 4A and 4B. The peak of the surface indicates a possible match with the target with the DRR or DE DRR in FIG. 4A or with the online image in FIG. 4B. The "sidelobes" are the values of the match score away from the peak vicinity, i.e., non-target locations in the search region. Whether or not a peak corresponds to the location of a target depends on how much it stands out relative to the sidelobes. Therefore, the decision variable that is compared with a threshold is the peak-to sidelobe ratio (PSR), which is defined as the peak value divided by the standard deviation of the sidelobes. This implies an adaptive threshold that is a constant multiple of the standard deviation of the sidelobes, hence keeping the false detection rate constant.

As an example, when the online image is generated, the image could be isolated as single radiograph, a sequence of radiographs, or a plurality of images. An online image angle is fed into a template selection, which is the result of a collection of templates that are created from a template generation. Once the online image, SE DRR, or DE DRR have been created, a template match gives an online image output, a SE DRR output, and/or a DE DRR output. Template matching is performed within a search region in order to compare the template with the treatment online image, DRR, or DE DRR. The result of the template matching is the visibility measure or visibility score for a specific angle. The visibility score is a numeric value resulting from a match score surface, where a peak to side lobe ratio is performed to identify an adaptive threshold. A correlation coefficient between the sources of data that are being compared produces a peak in the graph resulting in a real match.

Once the highest score value (either from the SE DRR or from the DE DRR) is selected and if the value meets the threshold requirement, then the angle is effective for tracking. The higher score value within the threshold provides an accurate location of the tumor and thus allows doctors to effectively track the location of the tumor in order to treat the correct part of the body. When the online images, SE DRRs, and/or DE DRRs are offset relative to each other in a template matching, they create side lobes. The ratio of the peak to the standard deviation of the side lobes, after excluding the peak, is a measure of visibility. With the visibility measure, a tumor can be detected and localized. However, if a match between the score values and the given threshold is not present, then the peak side lobe ratio is too low to predict the angle where the tumor is located; thus, the results cannot be tracked. The uses of online images, SE DRRs, and/or DE DRRs are contrasted with template matching to either fail or succeed at predicting, prior to the treatment, the angles in which a tumor can or cannot be seen.

Figure 5:
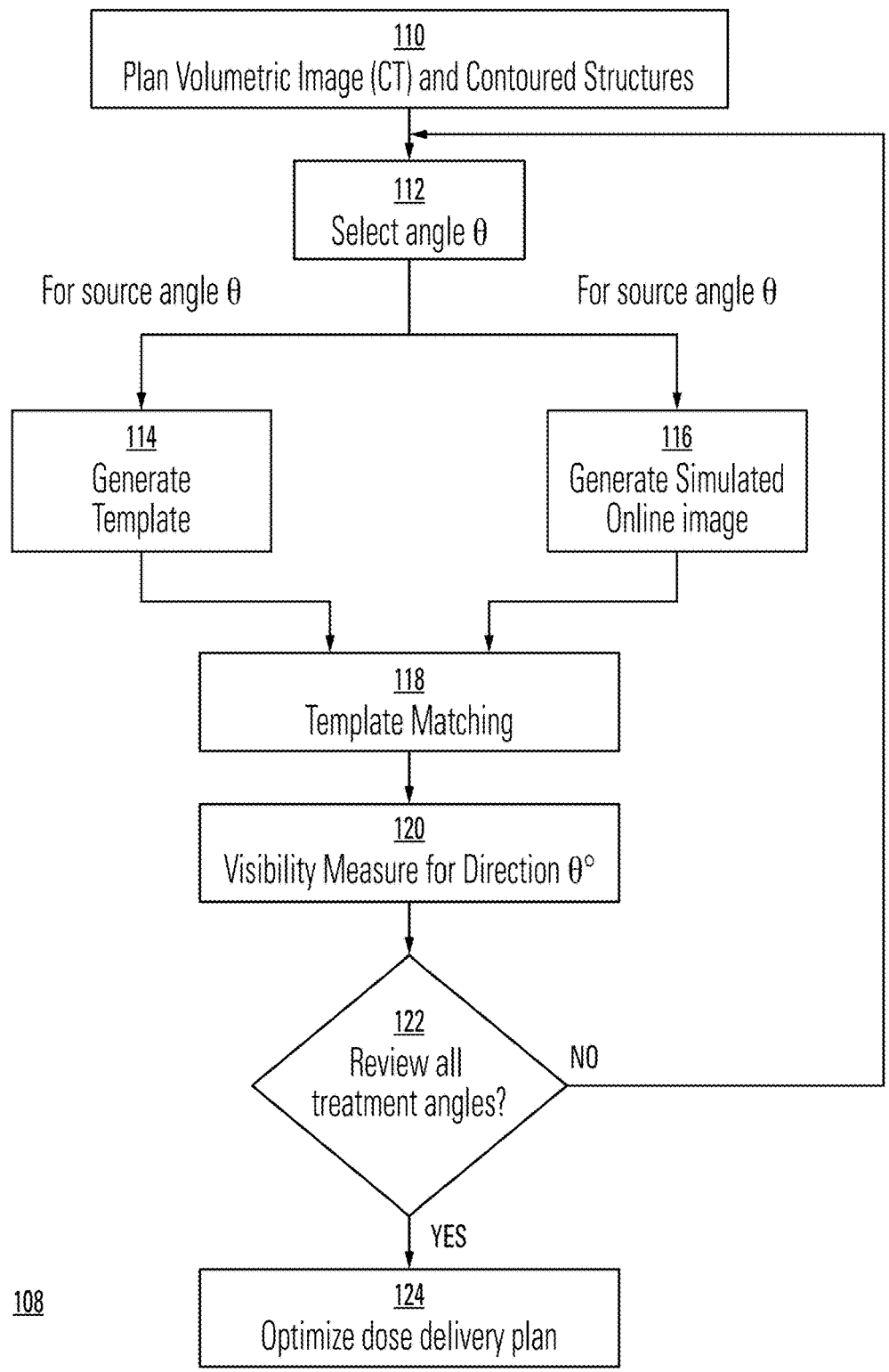
FIG. 5 is a flow diagram illustrating an embodiment of a plan volumetric image (CT) and contoured structures in accordance with the present invention.

FIG. 5 illustrates a plan volumetric image and contoured structures 110, in which a tumor visibility engine selects an angle theta (θ) at step 112. The angle θ is fed for source angle θ at step 114, in which the tumor visibility engine generates the template and at step 116 to generate a simulated online image. Template matching is performed at step 118 to compare the source angles in the generated template from step 114 and the source angles generated from the simulated online image from step 116. The result is of template matching 118 is a visibility measure for direction θ at step 120 for the stimulated online image. If the resulting visibility measure is sufficient, then the stimulated online image is classified as having a suitable angle for tracking the tumor at step 122. If this is the case, an optimized dose delivery plan can be implemented at step 124. If the resulting visibility measure is insufficient at step 122, then the stimulated online image is classified to be non-suitable for the treatment plan and an optimized dose delivery plan cannot be implemented at the selected angle θ.

Figure 6:
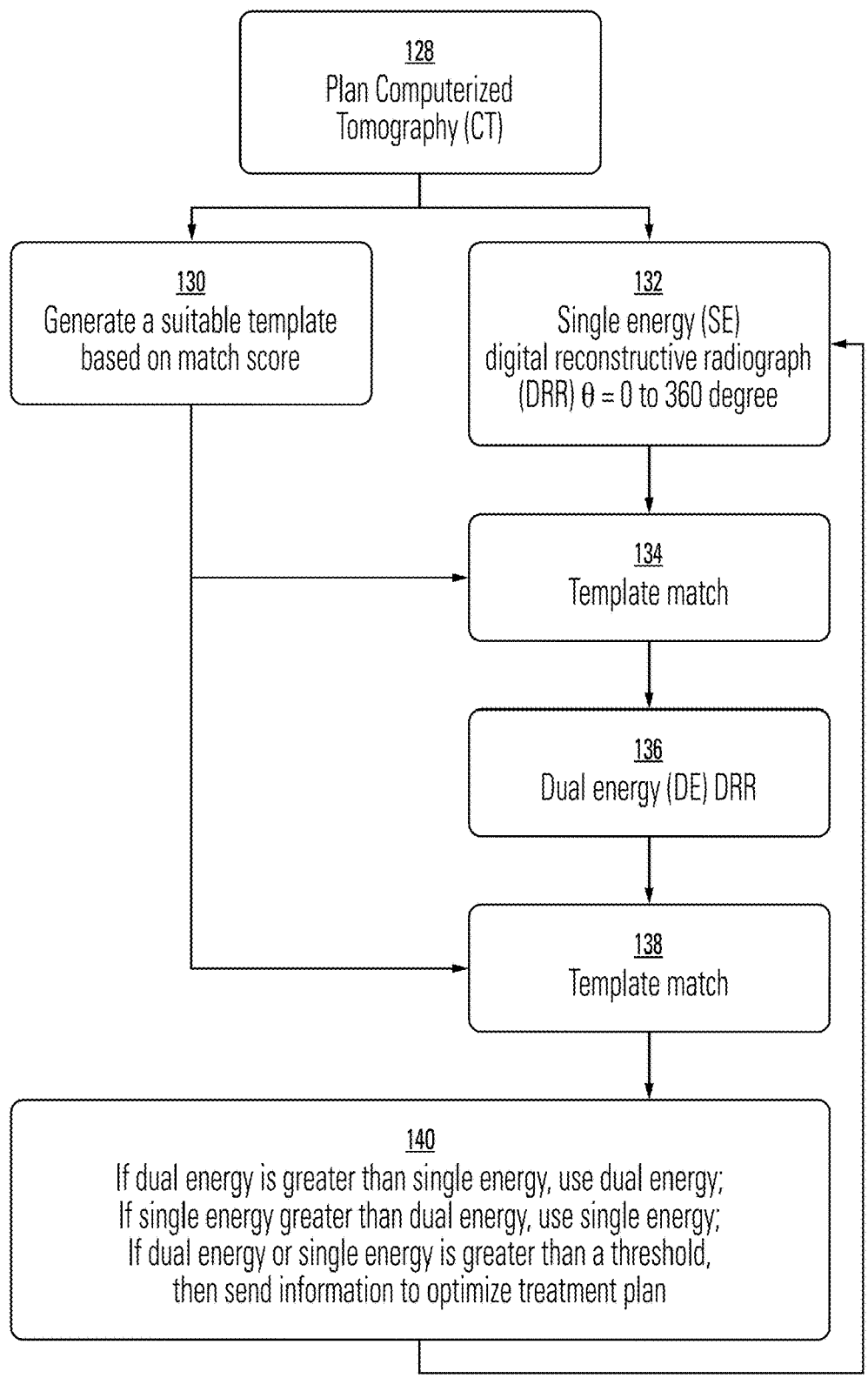
FIG. 6 is a block diagram illustrating a plan computerized tomography (CT) in accordance with the present invention.

FIG. 6 is a block diagram illustrating a plan CT in accordance with the present invention. FIG. 6 illustrates a plan CT 128, in which a tumor visibility engine generates a SE DRR and a DE DRR systematically and compares them through template matching to produce a match score. Template generation 130 evolves from the contours generated by the physicians. Once different angles thetas or angle sources have been selected to produce an image, the image is identified and an image angle is determined. The tumor visibility engine generates a template at step 130, SE DRR at step 132, and DE DRR at step 136. First, the SE DRR output is compared with template match at step 134. In this respect, a template match is compared with the SE DRR 132 to get a single energy score value because a SE DRR is being used. Second, a dual energy output is compared with a DE DRR at step 136 systematically. At this time, a template match at step 138 is compared with the DE DRR 136 output to get a dual energy score value because a DE DRR is being used. One of the advantages of a DE DRR 136 is that it can remove bony features, which can cause problems with the template matching. The result of the systematic process in template matching is a visibility measure for direction θ. At step 140, if the dual energy is greater than the single energy, the dual energy output is used. On the other hand, if the single energy is greater than the dual energy, the single energy output is used. If the dual energy or single energy is greater than a predetermined threshold, then the data is sufficient and suitable for tracking the tumor at the selected angle θ.

Figure 7:
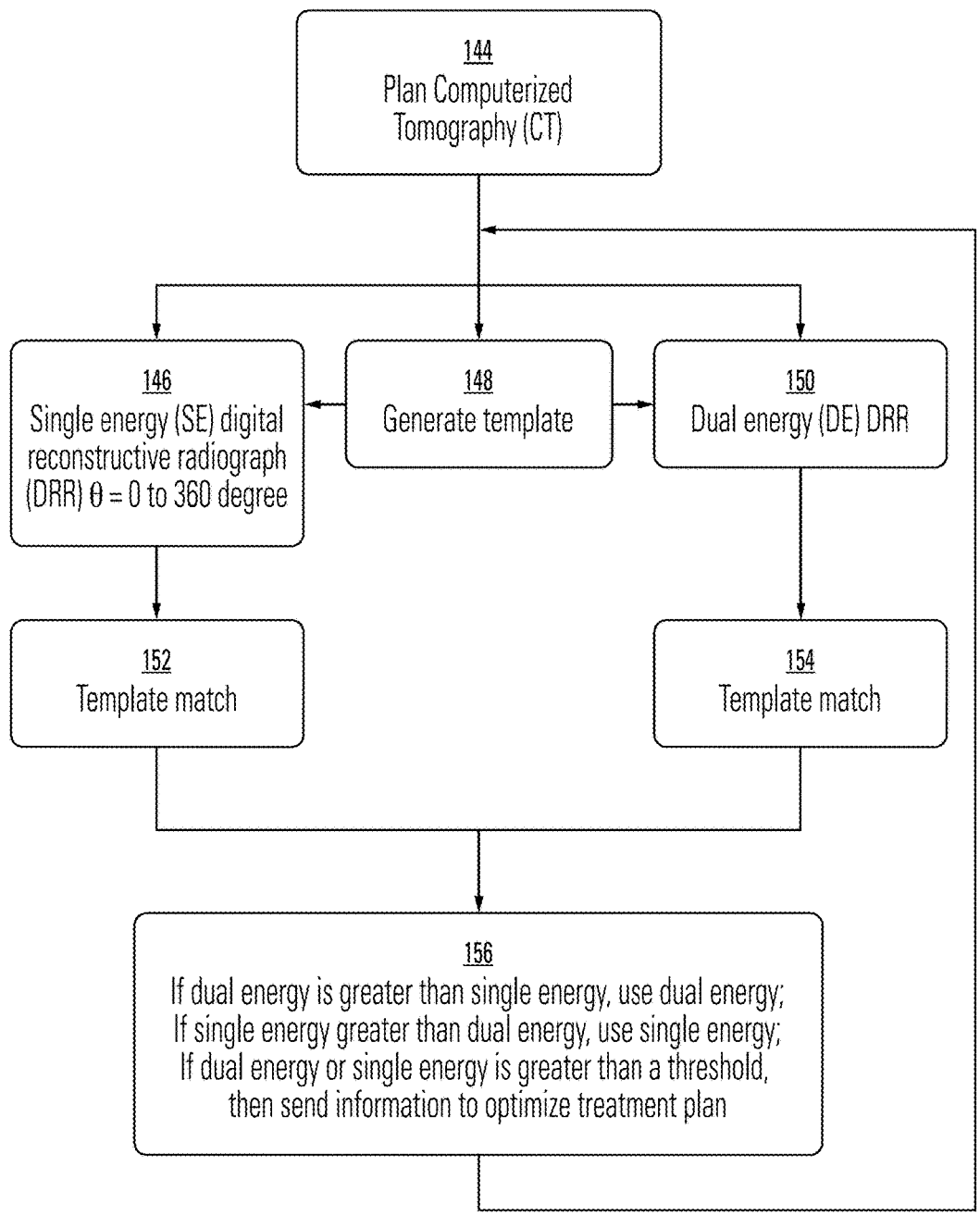
FIG. 7 is a block diagram illustrating a plan computerized tomography (CT) in accordance with the present invention.

FIG. 7 is a block diagram illustrating a plan CT 144, in which a tumor visibility engine generates a SE DRR and a DE DRR in parallel and compares them through template matching to produce a match score. The angle θ is fed for source angle θ and the tumor visibility engine generates a SE DRR at step 146, a template at step 148, and a DE DRR at step 150. Template matching is performed at the same time. At step 152, the SE DRR output is compared with the template match to get a single energy score value. At the same time, a dual energy output is compared with a DE DRR at step 154 to obtain a dual energy score value. The result of the parallel process in template matching is a visibility measure for direction θ. At step 156, if the dual energy is greater than the single energy, the dual energy output is used. On the other hand, if the single energy is greater than the dual energy, the single energy output is used. If the selected output is greater than a predetermined threshold, then the data is sufficient and suitable for tracking the tumor.

Figure 8:
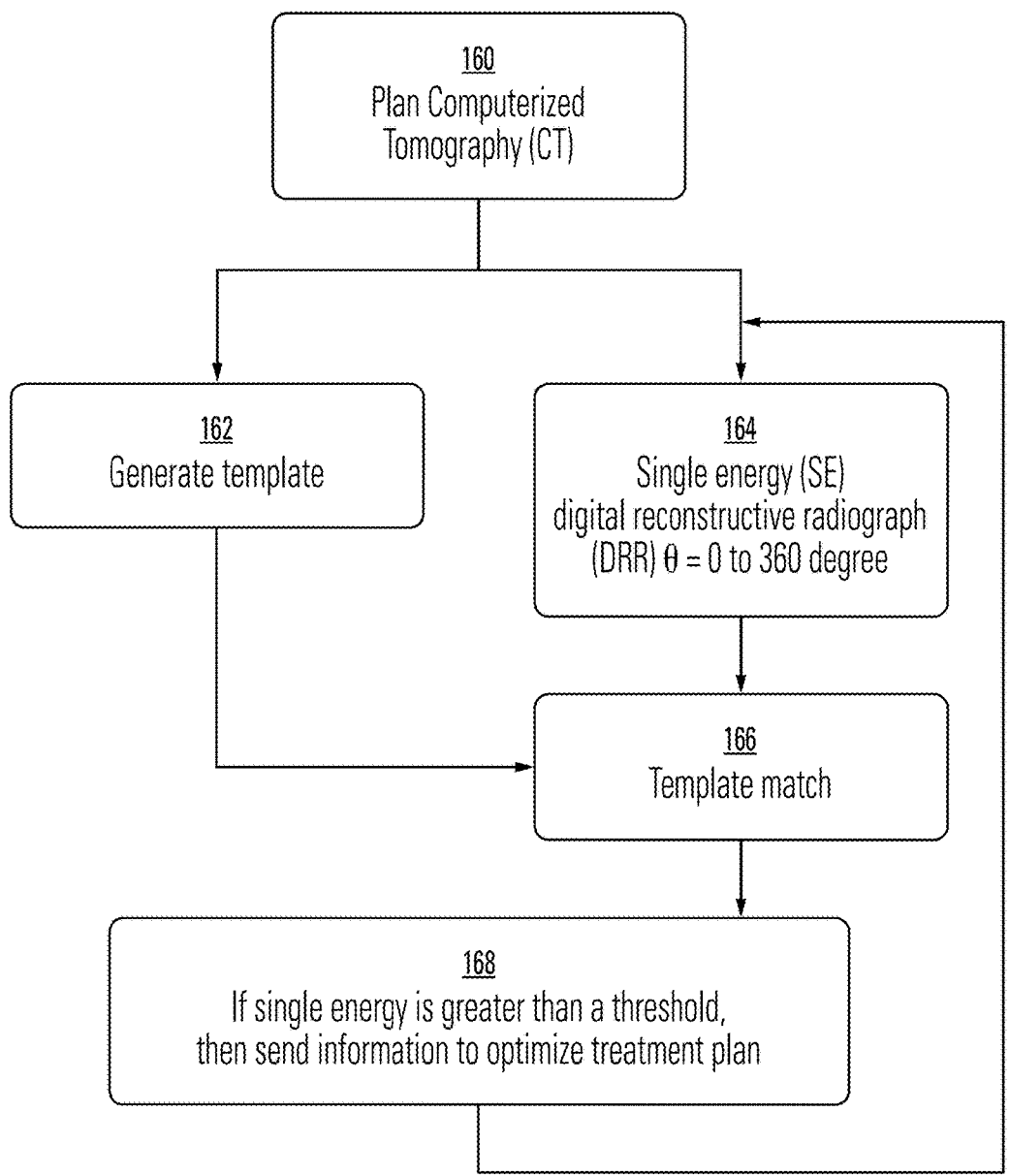
FIG. 8 is a block diagram illustrating a plan computerized tomography (CT) in accordance with the present invention.

FIG. 8 is a block diagram illustrating a plan CT 160, in which a tumor visibility engine only generates a SE DRR. The angle that is fed for source angle θ and the tumor visibility engine generates a SE DRR at step 164 and a template at step 162. At step 166, the SE DRR output is compared with the template match to get a single energy score value. The result of the template matching is a visibility measure for direction θ. At step 168, if the single energy output is greater than a predetermined threshold, then the data is sufficient and suitable for tracking the tumor.

Figure 9:
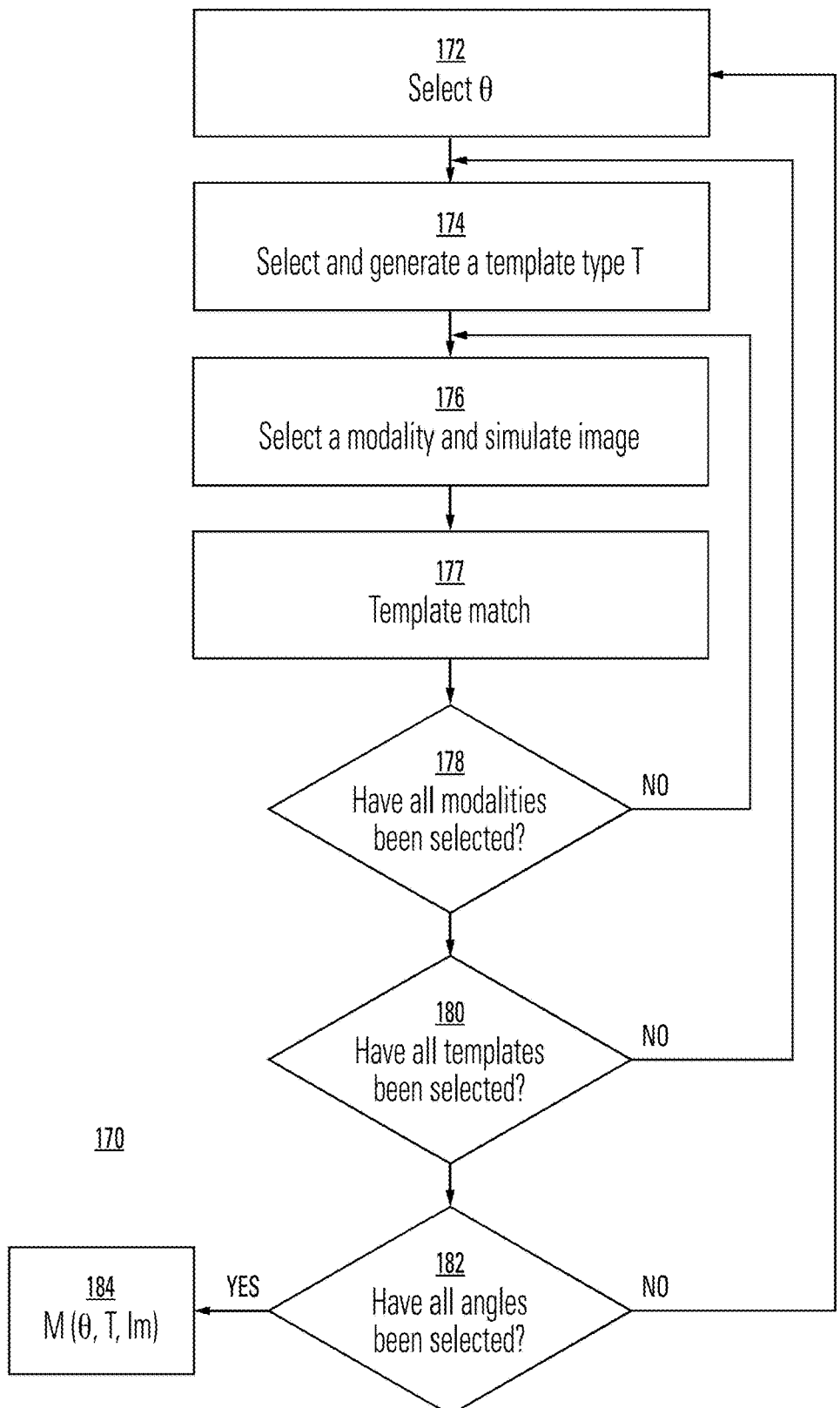
FIG. 9 is a block diagram illustrating the process of optimizing a template matching algorithm in accordance with the present invention.

FIG. 9 is a block diagram illustrating the process 170 of optimizing a template matching algorithm in accordance with the present invention. At step 172, the image-based localization optimizer engine 64 is configured to select an angle θ. At step 174, the image-based localization optimizer engine 64 is configured to select and generate a template type T. At step 176, the image-based localization optimizer engine 64 is configured to select a modality and simulate the image from a host of modalities including a SE, a DRR, or a DE DRR. At step 177, the image-based localization optimizer engine 64 is configured to determine the template match score with the selected image from step 176 and the selected template from step 174. At step 178, the image-based localization optimizer engine 64 is configured to determine if all modalities have been selected and processed. The process 170 returns to select another modality if the result in step 178 is that not all modalities have been selected and processed. If the determination result is in the affirmative, at step 180, the image-based localization optimizer engine 64 is configured to determine whether all templates have been selected and processed. The process returns to step 174 to select a different template if not all templates have been selected and processed. If all templates have been selected and processed at step 180, the process continues to step 182 to determine if all angles have been selected and processed. If not all angles have been selected and processed, the process returns to step 172 to select a different angle for processing. If all angles have been selected and processed, the image-based localization optimizer engine 64 is configured to generate an optimized output, M (θ, T, Im) at step 184.

Figure 11:
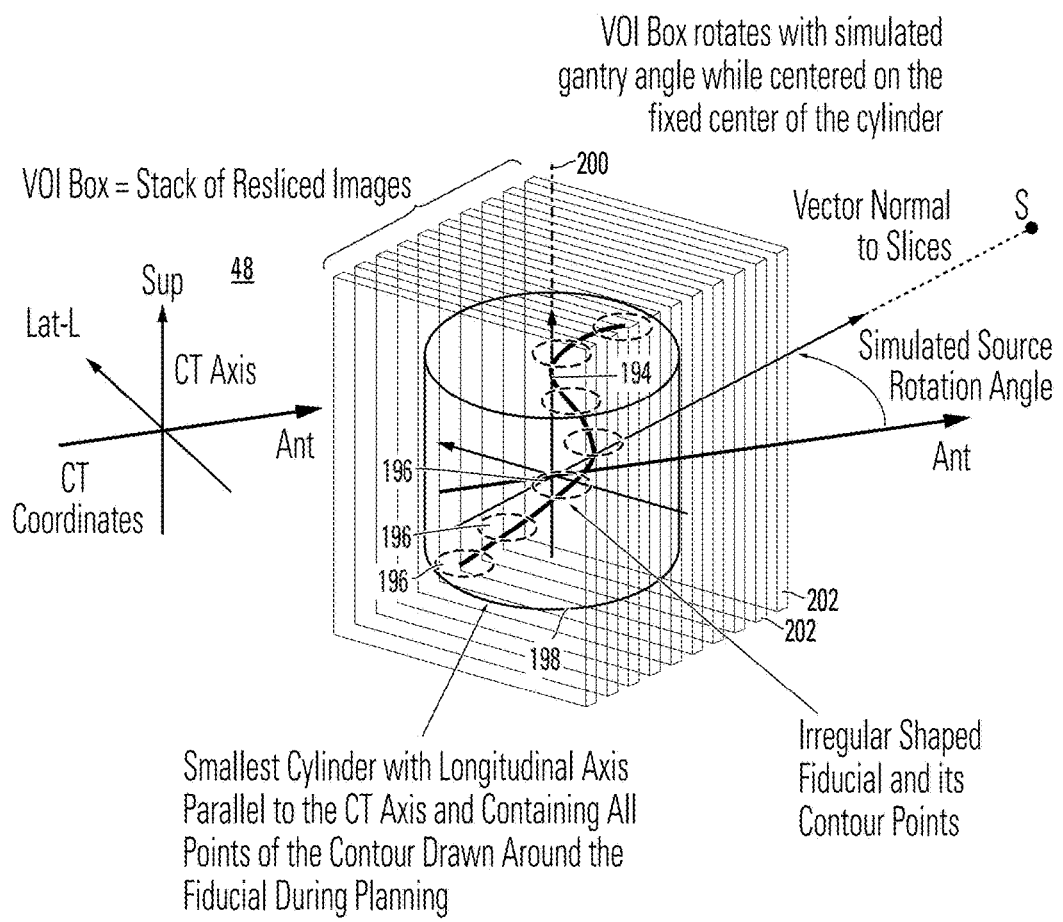
FIG. 11 is a block diagram illustrating a method of generating a template in accordance with the present invention.

FIGS. 10 and 11 illustrate a method 186 of generating a template in accordance with some embodiments. As shown in FIG. 10, the method 186 includes receiving an input from a user representing an identification of the object by the user (item 188). In some embodiments, the user may examine a volumetric image to identify object(s) of interest. The user may then create a contour around an object of interest by some means, such as by using a graphical user interface. In some embodiments, the created contour and/or data associated therewith may be an example of the input. In some cases, the volumetric image may include an image of an irregularly-shaped marker 194 (FIG. 11). In such cases, the user may examine different slices of the volumetric image to identify the marker 194 as it appears in the different slices, and then draw a contour 196 around the marker 194 in each of the different slices of the volumetric image. In some embodiments, item 188 in the method 186 of FIG. 10 may be accomplished by a device (e.g., a processor) receiving the input from the user that represents the identification of the object (e.g., marker 194). In other embodiments, the user input representing the identification of the object may be stored in a device, and item 188 may be accomplished by the same device that stores the input (e.g., the device itself may retrieve the stored input). In further embodiments, the user input representing the identification in a first device, and item 188 may be accomplished by a second device that retrieves the stored input from the first device.

Returning to FIG. 10, in the method 186, the input obtained from item 188 is used by a processor to determine a volume-of-interest (VOI) that includes voxels of the volumetric image (item 190). In some embodiments, the VOI includes the voxels that are within the contour(s) 196 drawn by the user in each of the slices of the volumetric image. In addition, in some embodiments, the VOI may include additional voxels that are outside the contour(s) 196. For example, in some embodiments, the VOI may include voxels from the volumetric image that are a certain prescribed distance from the drawn contour(s) 196. In other embodiments, the VOI may include voxels from the volumetric image that are within a defined three-dimensional spatial geometry. For example, as shown in FIG. 11, a cylindrical geometry 198 (an example of the VOI) may be defined based on the contour(s) 196, such that all of the voxels within the contour(s) 196 are within the cylindrical geometry 198. In some cases, the cylindrical geometry 198 may further be defined as having a circular cross section, and a longitudinal axis 200 that is perpendicular to the circular cross section and that is parallel to (or aligned with) a rotational axis of a gantry of an imaging device (e.g., the rotational axis 48 in the system 34 of FIG. 2). In other embodiments, the three-dimensional spatial geometry may have different shapes from the cylindrical geometry. In addition, in other embodiments, the three-dimensional spatial geometry may be defined using other criteria.

Returning to the method 186 of FIG. 10, next, the processor determines (e.g., calculates, generates, derives, etc.) a template using at least some of the voxels in the VOI 198 (Item 192). In some embodiments, the determination of the template may be accomplished by a processor performing a forward projection of the at least some of the voxels in the VOI 198. By means of no limiting examples, the forward projection may be a forward maximum intensity projection, a forward average projection, or a forward median projection, of the at least some of the voxels in the VOI 198. In some embodiments, before the forward projection is performed, the processor may also resample voxels in the VOI 198 into image planes 202 that are parallel to a plane of the input image. Thus, the re-sampling of the voxels in the VOI 198 may be based on the orientation of the input image. In such cases and depending the gantry angle at which the input image is generated, the orientation of the image planes 202 for the re-sampling of the voxels may be adjusted to correspond with the orientation of the input image.

As shown in the above embodiments, defining the VOI 198 is advantageous because it limits the number of voxels for processing (e.g., forward projection) to be a certain subset of the original volumetric image. This, in turn, results in the template image having a dimension that corresponds to the defined VOI 198. Accordingly, the resulting template image will have a dimension that covers the object(s) of interest, while other objects outside the VOI 198 will be excluded from being included in the template image. This is also advantageous in that it limits the template image to a size that is large enough for covering the object(s) of interest for tracking purpose. In some embodiments, the sizing of the template image is determined and accomplished automatically based on the input from the user.

In some embodiments, the template image determined from item 192 may be stored in a non-transitory medium for later processing. Alternatively or additionally, the template image may be displayed in a screen for allowing a user to see. In addition, in some embodiments, the processor may determine a plurality of template images using the above technique for different gantry angles. For example, the processor may determine a set of template images that correspond to gantry angles with 3° spacing. In one implementation, the processor may generate only half the number of template images (e.g., covering 180° range), and then generates the rest by flipping the template images horizontally. The template images may be stored in a non-transitory medium for later processing, and/or displayed in a screen for allowing a user to see. Furthermore, in some embodiments, any parameters and/or input that are involved in the method 186 may be stored in a non-transitory medium for later retrieval and/or processing. For examples, parameters and/or input that are used to define the VOI 198 may be stored in a non-transitory medium in some embodiments.

Figure 12:
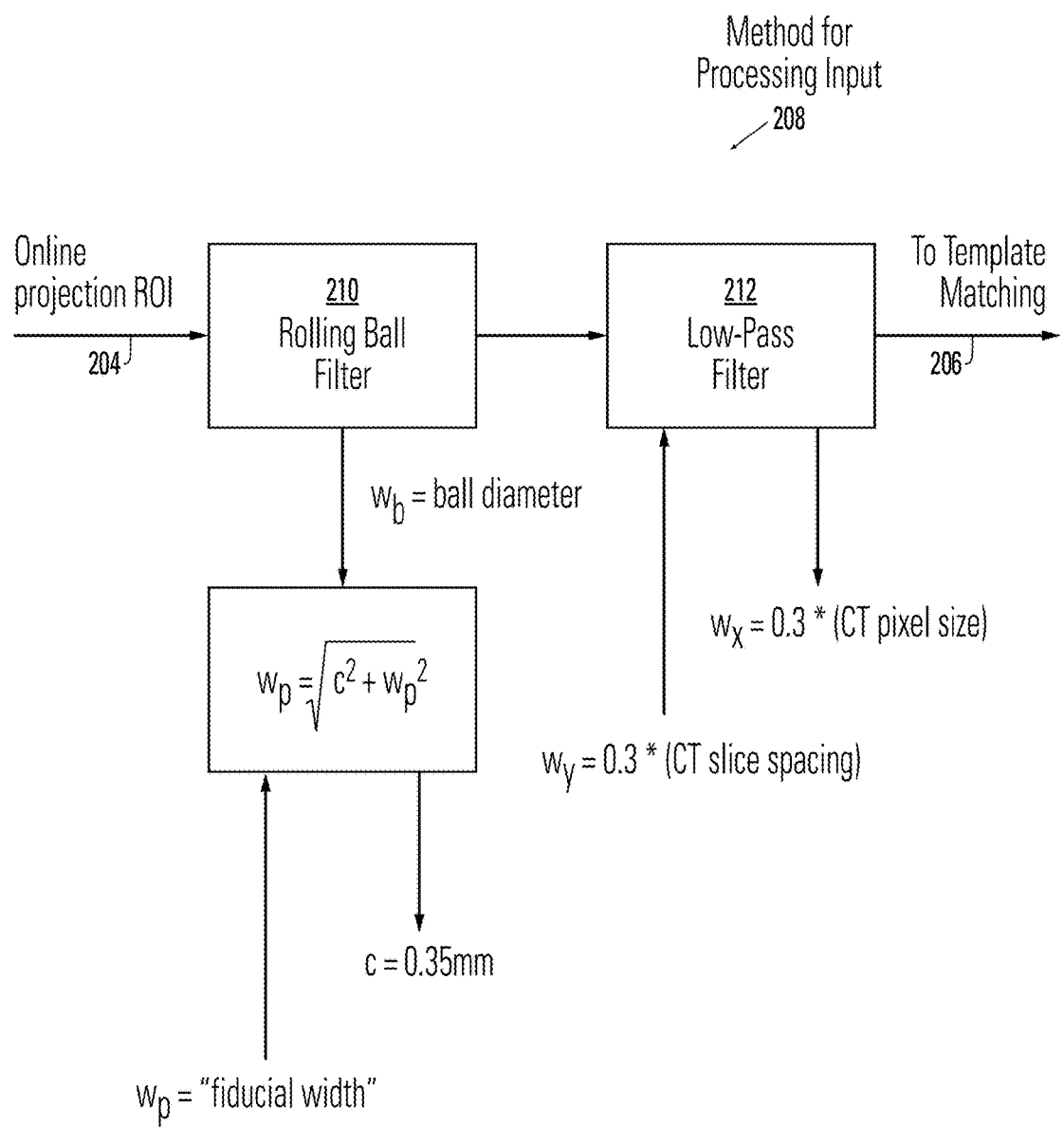
FIG. 12 is a diagram illustrating a method of processing an input image in accordance with some embodiments of the present invention.

FIG. 12 illustrates a method 208 for processing the input image 204 in accordance with some embodiments. As shown in the FIG. 12, a first filter 210 may be applied to the input image 204 to enhance an object in the input image 204. After the first filter 210 has been applied, a second filter 212 may be applied so that the processed image 206 has a degree of resolution that corresponds (e.g., matches or closely resembles) with that of the template image.

In the illustrated embodiments, the first filter 210 is a rolling ball filter. In one implementation, a rolling ball filter may be defined at least partially by a ball diameter $wb=(c2+wp2)\cdot\frac{1}{2}$, wherein wp is a fiducial width (e.g., a width, such as a cross sectional dimension, of the marker 194), and c may be any constant. In some embodiments, wp may be 0.35 mm for a Visicoil wire that is not coiled up, or may be 2.0 mm for a Visicoil wire that is coiled up. In other embodiments, wp may be 3.0 mm for a coiled up embolization coil. In further embodiments, wp may be a diameter of a cylindrical gold seed, such as 0.8 mm. It should be noted that wp should not be limited to the above examples, and that wp may have other values that are different from the above examples. In addition, in some embodiments, c may be a value that is anywhere between 0.1 mm and 1 mm, and more preferably, between 0.2 mm and 0.5 mm, and more preferably, between 0.3 mm and 0.4 mm (e.g., 0.35 mm). In other embodiments, c may be other values different from those described. In some embodiments, the rolling ball filter may be applied to the input image 204 to enhance an object (e.g., the marker 194, or a tissue structure) relative to its surrounding objects. In other embodiments, the rolling ball filter may be applied to the input image 204 to enhance a boundary of the object (e.g., a boundary of tissue structure).

In addition, in the illustrated embodiments, the second filter 212 is a low-pass filter. In one implementation, the low-pass filter may be defined at least partially by two parameters wx, wy. The parameter wx is used to configure the input image 204 so that the processed image 206 has a resolution in the x-direction that corresponds with a pixel size of the volumetric image (that was used to generate the template image). The parameter wy is used to configure the input image 204 so that the processed image 206 has a resolution in the y direction that corresponds with a slice spacing of the volumetric image (that was used to generate the template image). In some embodiments, wx may be determined as a constant (e.g., 0.3, or any of other values) times a pixel size in the volumetric image. In addition, in some embodiments, wy may be determined as a constant (e.g., 0.3, or any of other values) times a slice spacing of the volumetric image. Furthermore, in some embodiments, the low-pass filter may be a Gaussian shaped low-pass filter. In one implementation, the Gaussian shaped low-pass filter may be specified by 1 standard deviation widths in the x direction and the y-direction with respect to the input image 204.

It should be noted that there may be other parameter(s) for defining the low-pass filter in other embodiments. For example, in addition/alternative to the parameters described above, other filter parameter(s) may include Source Axis Distance (SAD), Source Detector Distance (SDD), detector pixel size, or combination thereof.

In other embodiments, each of the first filter 210 and the second filter 212 may be any of other types of filters that are different from the examples described.

Figure 13:
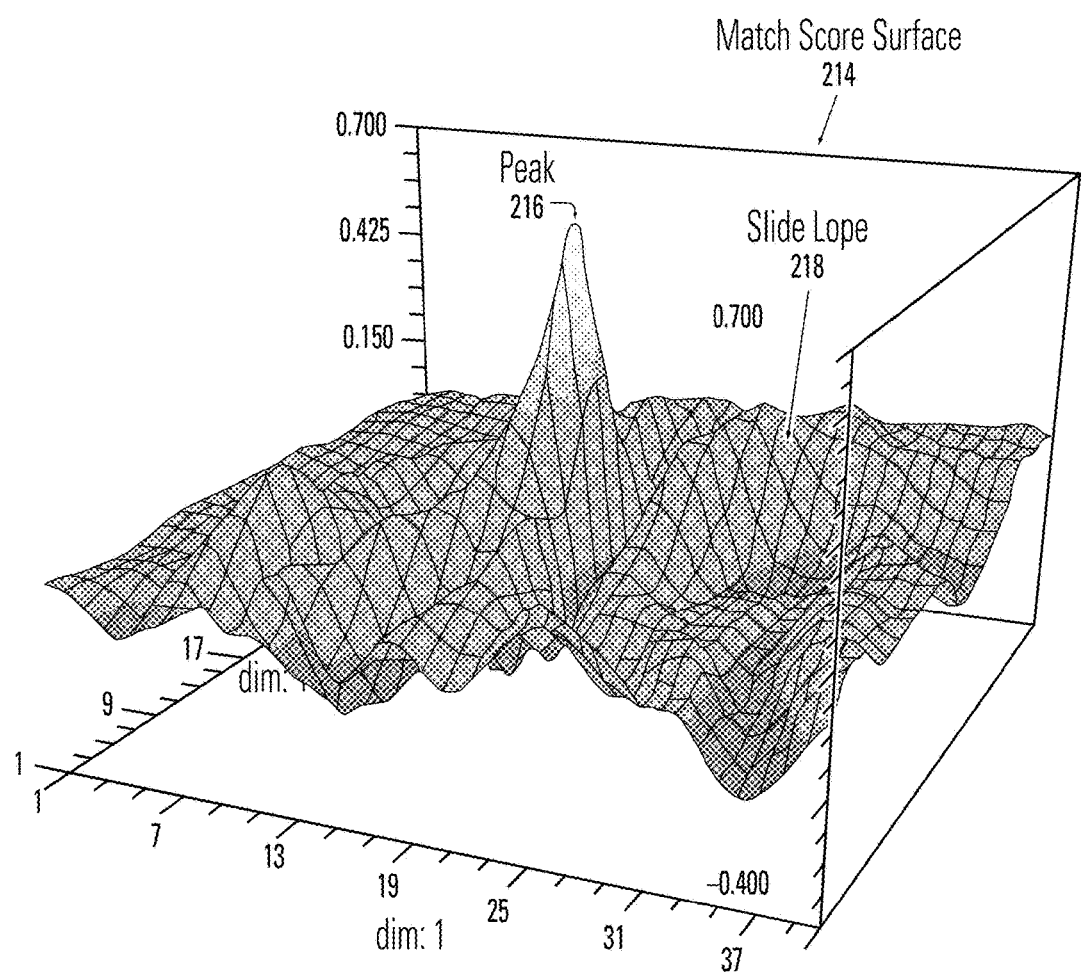
FIG. 13 is a graph illustrating an example of a match score surface in accordance with some embodiments of the present invention.

As shown in FIG. 13, the match scores may define a match score surface 214 over a search region. As shown in the figure, the match score surface 214 may have a peak 216 and at least one side lobe 218. In some embodiments, the values in the match score surface 214 may optionally be normalized, with the highest peak 216 having a value of 1.0.

In some cases, the fact that there is a peak in the match score surface 214 may not represent that the object(s) of interest is in the processed image 206. In other words, the peak 216 in the match score surface 214 may not represent a "true" match between the processed image 206 and the template image. This is because the above technique of determining the match score surface 214 will always result in a peak 216 in the match score surface 214, regardless of whether there is a "true match." Thus, in some embodiments, it may be desirable to determine whether the peak 216 represents a match between the processed image 206 and the template image 220.

To accomplish this, in some embodiments, the processor may determine how much the peak 216 stands out relative to the side lobe(s) 218. For example, in one implementation, the processor may be configured to determine a peak-to-side lobe ratio by dividing the value of the peak 216 by the value of the side lobe 218. In another embodiment, the processor may determine a standard deviation of the side lobe(s) 218, and determine a peak-to-side lobe ratio by dividing the value of the peak 216 by the standard deviation of the side lobe(s) 218. After the peak-to-side lobe ratio is determined, the processor may then compare the peak-to-side lobe ratio with a threshold to determine whether there is a match between the processed image 206 and the template image. If the peak-to-side lobe ratio exceeds the threshold, then the processor may determine that the target (object of interest) is present. Otherwise, the processor may determine that the target is absent. If the target is present, the position of the peak 216 may be used as the position of the target. In some embodiments, the threshold may be determined based on side lobe statistics for a given image, such as that shown in FIG. 14 and discussed herein. Alternatively, the threshold may be determined based on side lobe statistics for multiple images.

In addition, as discussed, in some embodiments, the processor may compare the processed image 206 with several template images that are adjacent (in terms of orientation/gantry angles) next to the processed image 206 to account for slight rotation of the object of interest. In such cases, for each of the template images, the processor may determine a corresponding peak-to-side lobe ratio. The processor may also select the template image having the highest peak-to-side lobe ratio as the matched template image, and use the position of the peak 216 in such template image as the position of the target.

In one or more embodiments, the processor may be automatically configured to identify the side lobe(s) 218. For example, in some embodiments, the processor may be configured to exclude the peak 216 and its vicinity from the match score surface 214, and the remaining surface will have the side lobe(s) 218, and not the peak 216. In some embodiments, the processor may determine a mask to exclude the peak 216. For example, the processor may determine the mask by cross correlating the template image with itself at different offsets to obtain an autocorrelation surface. Then the processor identifies locations where the autocorrelation surface exceeds a threshold value. For example, the threshold value may be anywhere between 0.1 and 0.3, or more preferably anywhere between 0.15 and 0.25 (e.g., 0.2). All values in the match score surface 214 exceeding the threshold value will be parts of an exclusion zone. When the exclusion zone is applied to the match score surface 214, the peak 216 and its vicinity will be removed.

Alternatively, the processor may identify locations where the autocorrelation surface is below a threshold value. For example, the threshold value may be anywhere between 0.1 and 0.3, or more preferably anywhere between 0.15 and 0.25 (e.g., 0.2). All values in the match score surface 214 that are below the threshold value will be parts of an acceptance zone. When the acceptance zone is applied to the match score surface 214, the side lobe(s) 218 will remain as parts of the remaining surface, while the peak 216 and its vicinity will be removed. In such cases, the mask represents the acceptance zone, not the exclusion zone.

In one or more embodiments, the mask (which may represent an exclusion zone or an acceptance zone) may be stored in a non-transitory medium. For example, the mask may be saved as a list of (X, Y) coordinates, with (0, 0) referenced to the peak position.

Figure 14:
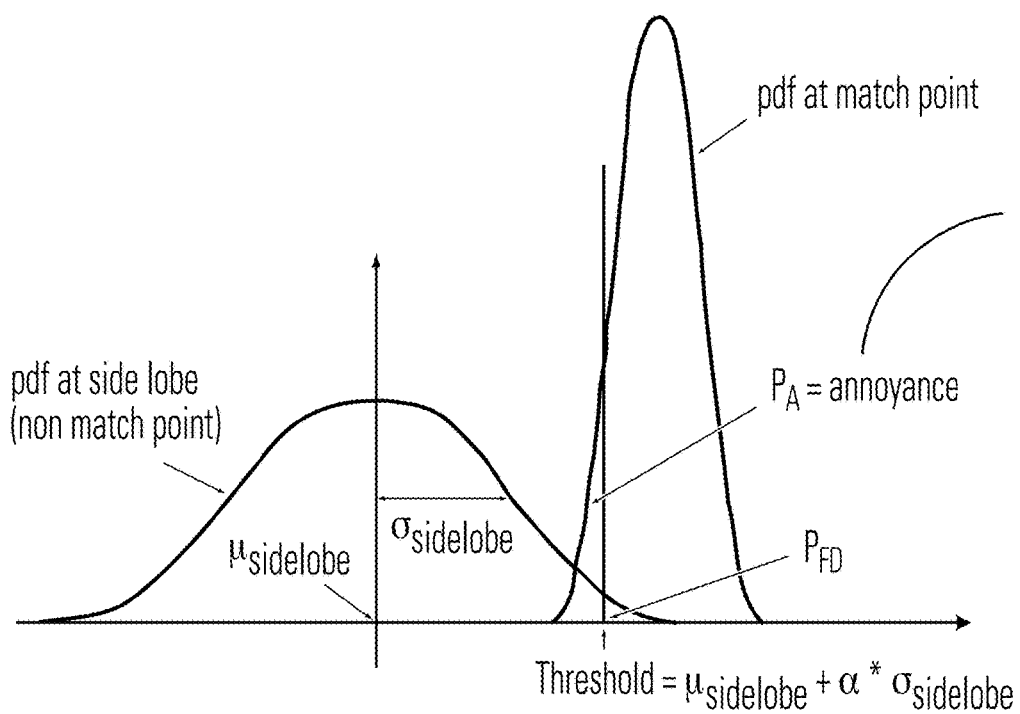
FIG. 14 is a graph illustrating a threshold parameter that affects false detection probability and probability of missing a target.

As shown in FIG. 14, the threshold determines the probability PFD of falsely detecting a target at a non-target point in the search region. The threshold also determines the probability PA of missing a target that is in fact present.

In the above embodiments, the object(s) of interest has been described with reference to the marker 194. The marker 194 may have an elongate configuration, a spherical configuration, an elliptical configuration, a random three-dimensional configuration, or any of other configurations. In other embodiments, the object(s) of interest may be a plurality of markers. In such cases, the VOI (e.g., the cylindrical geometry 198) may include voxels that are within contours 196 of the markers drawn by the user in each of the slices of the volumetric image. Accordingly, the resulting template image(s) obtained from the method 186 of FIG. 10 will include images of the markers 194. When such template image(s) is used in the template matching process, the processed image 206 will be compared with the template image(s) based on the group of markers 194 as if they are a single object.

Figure 15:
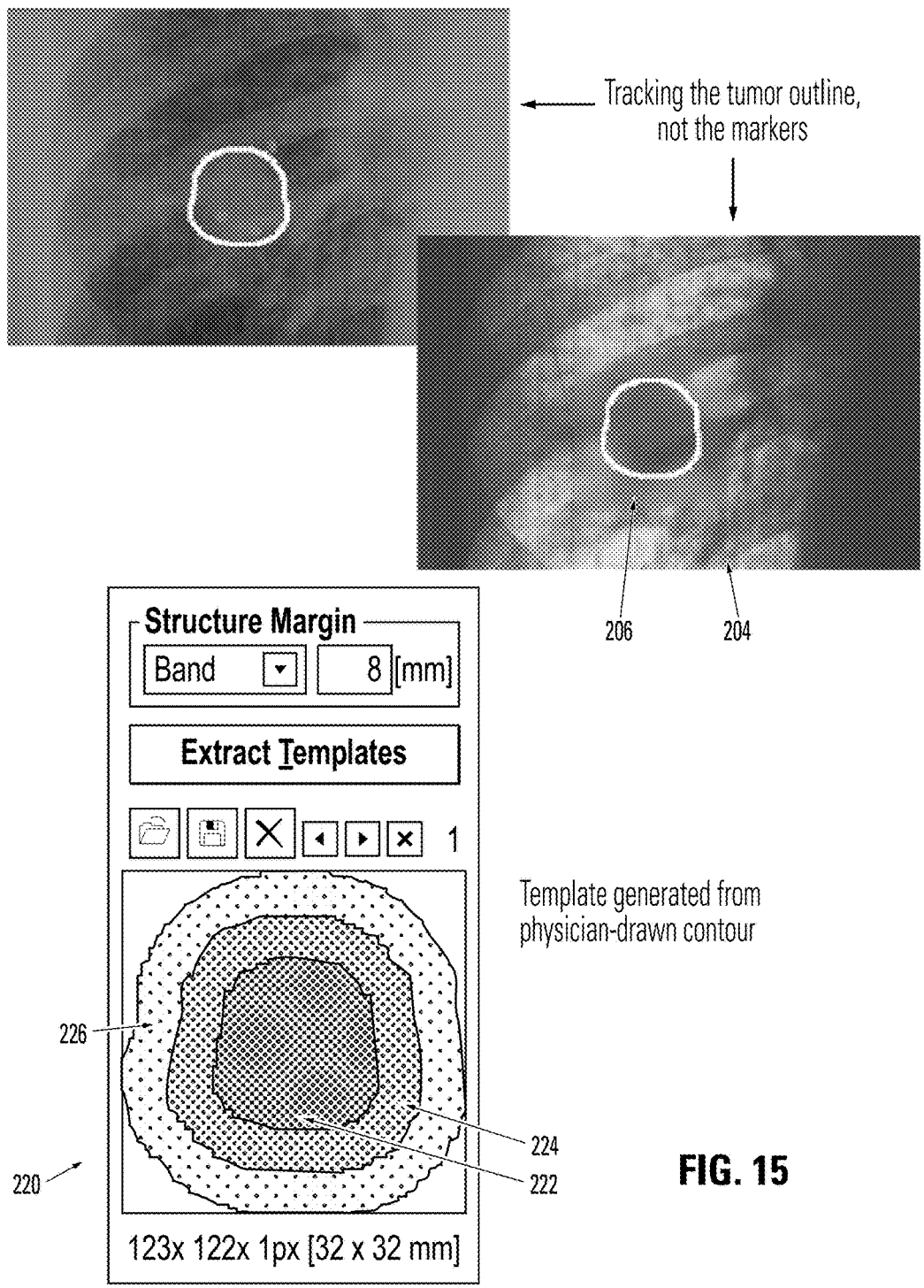
FIG. 15 is a graphic illustrating a technique for performing tracking without using implanted markers.

In addition, in other embodiments, the object(s) of interest may be a tissue structure (marker less fiducial). In such cases, the template image(s) may be generated so that it has features that correspond with the tissue structure. For example, as shown in FIG. 15, in some embodiments, the template image 220 may include a region 222 having a shape that resembles the tissue structure. The template image 220 may also include a first layer/region 224 surrounding the region 222, and a second layer/region 226 surrounding the first layer/region 224. As shown in the FIG. 15, the regions 222, 224, 226 in the template image 220 have different respective colors/gray-scales.

Various techniques may be employed to generate the template image 220. In some embodiments, a person may review slices of a volumetric image, and identify object of interest. The person may then create contours around the object of interest in the respective slices of the volumetric image. In some embodiments, the processor (e.g., the processor 54, or another processor) may be configured to receive the created contours as input 212 from the user, and automatically create a three-dimensional model based on the input 212. In some embodiments, the three-dimensional model may have a volume that is defined at least partially by the contours drawn by the person. For example, the volume of the three-dimensional model may have a surface that intersects the created contours. In addition, in some embodiments, the three-dimensional model may further include a first layer created automatically by the processor so that the first layer surrounds the volume, and a second layer created automatically by the processor so that the second layer surrounds the first layer. The first layer may have a first predetermined thickness, and the second layer may have a second pre-determined thickness. Also, the processor may assign all voxels inside the volume to have a first color/gray-scale (like the color shown in the region 222 in the template 214 in FIG. 15), all voxels inside the first layer to have a second color/gray-scale (like the color shown in the region 224 in the template 214), and all voxels inside the second layer to have a third color/grayscale (like the color shown in the region 226 in the template 214). After the three-dimensional model is created, it may be stored in a non-transitory medium for later processing.

During use, the input image 204 is received by the processor. In order to cross correlate with the input image 204, the processor re-slices the three-dimensional contour in order to make a two dimensional contour parallel to the input image plane. The re-slicing may, for example, be through a treatment isocenter (e.g., the center point of the tumor as identified by the user during planning). To match the geometry of the input image, the processor may be forward configured to project this two-dimensional contour. Then the processor may generate the two layers 222, 224 surrounding the contour in the forward projected contour image, thus resulting in a two-dimensional template (like the template 214 shown in the example of FIG. 13).

In some embodiments, when performing the method 200 based on marker less fiducial(s) (e.g., tissue structure), the input image 204 may be processed so that the processed image 206 looks like the template image 220. For example, in the image processing 204/208, the first filter 210 may be applied to highlight a boundary of tissue structure, and the second filter 212 may be applied to smooth the features inside the boundary of the tissue structure. As shown in the example of FIG. 15, using such technique, the input image 204 maybe processed to achieve a processed image 206 having a smeared feature, so that the processed image 206 resembles the template image 220. In some embodiments, the first filter 210 may be a rolling ball filter, and the second filter 212 may be a low-pass filter (e.g., a median filter, an average filter, etc.). In other embodiments, the first filter 210 may be another type of filter. For example, in some embodiments that involve marker less fiducial(s), the first filter 210 may be any type of filter that is capable of enhancing a boundary of tissue structure. In addition, for marker less fiducial(s), the second filter 212 may be a median filter in one implementation.

After the input image 204 is processed to obtain the processed image 206, and after the template image 220 has been obtained, the processed input image 206 is then compared with the template image 220 in the template matching process 206, like that described previously.

In other embodiments, the input image 204 may be a DTS image that is made from multiple angularly adjacent projections rather than a single projection. Digital tomosynthesis image is an image (e.g., volumetric image) that is reconstructed using projection images, wherein the number of projection images involved may be less than those for a CT image are. In such cases, the image processing 204 is optional, and the DTS input image 204 itself (e.g., a slice of the DTS input image 204) may be used for comparison with the template 214. In other embodiments, the image processing 204 may be performed to enhance a feature in the DTS input image 204 before the enhanced input image is compared with the template 214. The template 214 for comparison with the input image 204 may be a DTS image constructed from a CT volumetric image 110. In such cases, the DTS image that forms the template 214 may be considered an "artificial" DTS image because it is not constructed according to conventional technique in which a DTS image is reconstructed from a plurality of projection images.

Figure 16A:
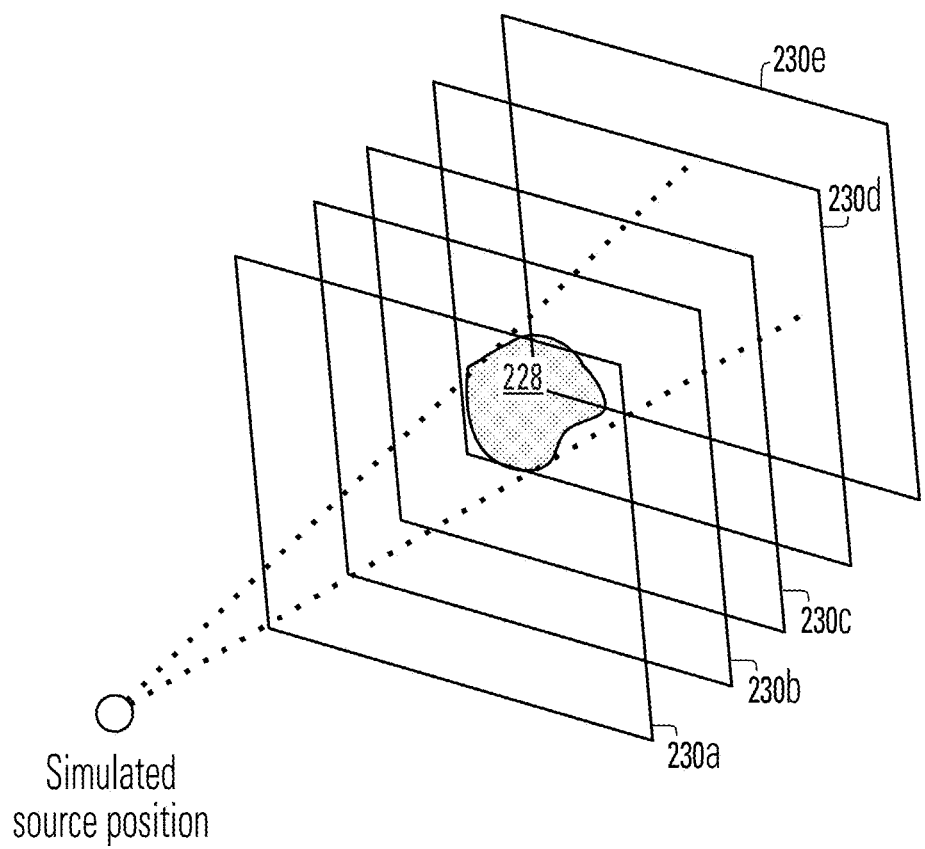
FIG. 16A illustrates a technique for generating a digital tomosynthesis image using a volumetric image in a simulated source position in accordance with some embodiments of the present invention.
Figure 16B:
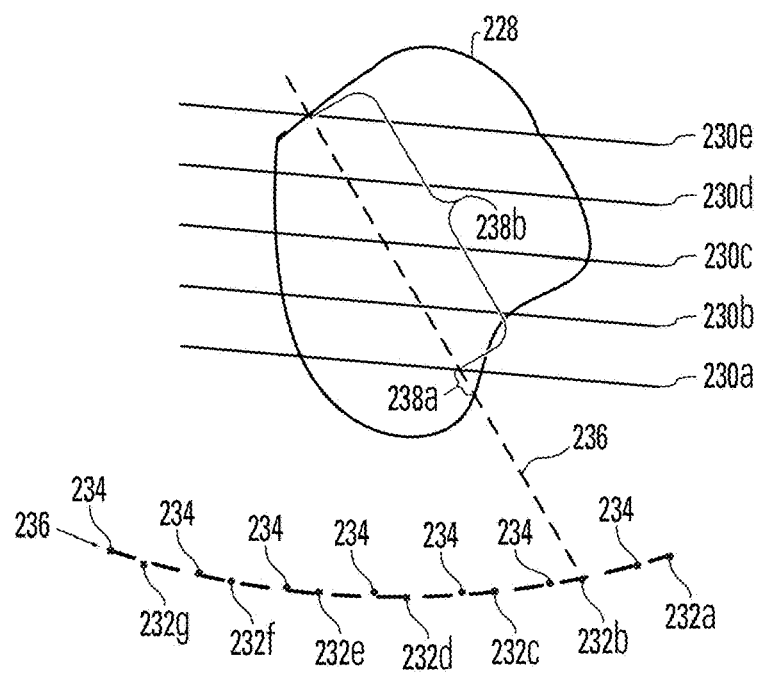
FIG. 16B and FIG. 16C are also examples of the technique for generating a digital tomosynthesis image by using volumetric image in a simulated source position.

Various techniques may be used to obtain a set of artificial DTS images from a volumetric CT image. In some embodiments, the processor (e.g., the processor 54, or another processor) is configured to computationally forward project voxels (e.g., those in a region of interest as defined by a user) in the volumetric image 110 onto a set of intermediate planes to create image slices 230a-230e (FIG. 16A). In one technique, when performing the forward projection to create the image slices 230a-230e, the processor may mathematically move a simulated source along a trajectory (e.g., an arc path) partially around an object in the volumetric image 110 to different positions that correspond with the angular spacing of the projections used to form the online DTS image 204. Such technique is illustrated graphically in FIG. 16B. As shown in the FIG. 16B, the forward projection is performed from different positions 232a-232g with angular spacing 234. In some embodiments, the angular spacing 234 may be equal to the angular spacing of the projections used to form the online DTS image 204. In other embodiments, the angular spacing 234 may be different from (e.g., greater than, or less than) the angular spacing of the projections used to form the online DTS image 204. To create a slice 230 (e.g., 230a), forward projection is performed from the different positions 232a-232g onto the plane of the slice 230 (e.g., the plane of slice 230a). For example, when performing forward projection from position 232b onto the plane of the image slice 230a, all points along the projection path 236 (including points 238a in front of the plane of the image slice 230a, and points 238b in the back of the plane of the image slice 230a) through the voxels of interest in the volumetric image 110 are projected onto the plane of the image slice 230a. Although one projection path 236 is shown in the example, it should be understood that there may be multiple projection paths 236 for any given position 232 that extend from the position 232 and that intersect the plane of the slice being created, thereby creating a two dimensional forward projection image onto the plane of the slice being created for any given position 232. Forward projections are also performed from other positions (e.g., 232a, 232c-232g) onto the plane of the image slice 230a. The forward projections at the plane of the image slice 230a are then summed to create the image slice 230a. The same technique may be repeated to create other image slices 230b-230e. Although five image slices 230a-230e are shown in the example, in other embodiments there may be more than five image slices 230 or fewer than five image slices. In some cases, the image slices 230a-230e may be considered as corresponding to an intermediate stage of back projecting in a DTS reconstruction algorithm.

In some embodiments, the mathematical moving of a simulated source may be considered to have been performed by the processor when the processor has performed forward projection from multiple angular positions. In addition, in some embodiments, when performing the forward projection, the arc center for the trajectory 236 of the simulated source may be the same as the arc center for the trajectory for obtaining the online DTS image 204. In addition, in some embodiments the arc length for the trajectory of the simulated source may be the same as the arc length for the trajectory for obtaining the online DTS image 204. In other embodiments, the arc length for the trajectory of the simulated source may be different from (e.g., longer than) the arc length for the trajectory for obtaining the online DTS image 204 for achieving better depth resolution.

In some embodiments, after the image slices 230a-230e are formed, the image slices 230a-230e themselves may be used as templates 214. In other embodiments, the image slices 230a-230e may be deblurred to create respective deblurred image slices, and the deblurred image slices are then used as templates 214.

Figure 16C:
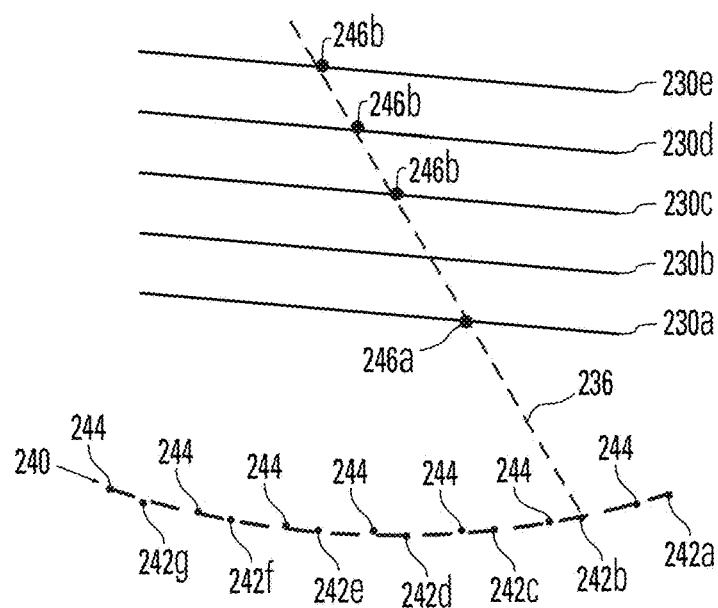

Various techniques may be employed to de-blur the image slices 230a-230e. In some embodiments, to de-blur a slice 230, the processor may determine a blur image contributing from objects in other slices, and may subtract this blur image from the slice 230 being deblurred. For example, to deblur image slice 230b, other slices 230a and 230c-230e are forward projected onto the plane of the image slice 230b, and are then summed to create a blur image for the image slice 230b. FIG. 16C illustrates this technique. As shown in the FIG. 16C, to create a blur image for slice 230b, the processor (e.g., the processor 54, or another processor) is configured to computationally forward project pixels in the other image slices 230a and 230c-230e onto the plane of the image slice 230b. In one technique, when performing the forward projection to create the blur image, the processor may mathematically move a simulated source along a trajectory 240 (e.g., an arc path) partially around an object of interest to different positions that correspond with the angular spacing of the projections used to form the online DTS image 204. As shown in the FIG. 16C, the forward projection is performed from different positions 242a-242g with angular spacing 244. In some embodiments, the angular spacing 244 may be equal to the angular spacing of the projections used to form the online DTS image 204. In other embodiments, the angular spacing 244 may be different from (e.g., greater than, or less than) the angular spacing of the projections used to form the online DTS image 204. In addition, in some embodiments, the angular spacing 244 for generating the blur image may be the same as the angular spacing 234 for generating the image slices 230. In other embodiments, the angular spacing 244 for generating the blur image may be different from the angular spacing 234 for generating the image slices 230. To create the blur image for the image slice 230b, forward projection is performed from the different positions 242a-242g onto the plane of the image slice 230b. For example, when performing forward projection from position 242b onto the plane of the image slice 230b, all points along the projection path 236 (including point 946a in front of the plane of the image slice 230b, and point 246b in the back of the plane of the image slice 230b) at the different image slices 230a and 230c-230e are projected onto the plane of the image slice 230b. Although one projection path 236 is shown in the example, it should be understood that there may be multiple projection paths 236 for any given position 242 that extend from the position 242 and that intersect the plane of the slice being deblurred, thereby creating a two dimensional forward projection image onto the plane of the slice being deblurred for any given position 242. Forward projections are also performed from other positions (e.g., 242a, 242c-242g) onto the plane of the image slice 230b. The forward projections at the plane of the image slice 230b are then summed to create the blur image for the image slice 230b. The above technique may be repeated to create corresponding blur images for the other respective image slices 230a and 230c-230e.

In some embodiments, the mathematical moving of a simulated source during the deblurring process may be considered to have been performed by the processor when the processor has performed forward projection from multiple angular positions. In addition, in some embodiments, in the deblurring process the arc center for the trajectory of the simulated source may be the same as the arc center for the trajectory for obtaining the online DTS image 204. In addition, in some embodiments, the arc length for the trajectory of the simulated source may be the same as the arc length for the trajectory for obtaining the online DTS image 204. In other embodiments, the arc length for the trajectory of the simulated source may be different from (e.g., longer than) the arc length for the trajectory for obtaining the online DTS image 204.

After the blur image is obtained, the processor then subtracts the blur image from slice 230b to de-blur the slice 230b. The same process is performed to deblur the other slices (e.g., 230a, and 230c-230e) in the set to result in a set of deblurred image slices. In some embodiments, the deblurred image slices may be stored as the templates 214 in a non-transitory medium for later processing (e.g., template matching with the online image 204).

The above technique results in a set of deblurred slices 230a-230e that form a set of templates 214 for a given gantry angle. In some embodiments, the processor may select a center one of the deblurred slices 230a-230e (or one of the slices that is the closest to the center) to use for comparison with the online DTS image 204 (e.g., a corresponding slice in the online DTS image 204). In other embodiments, the processor may compare multiple slices of the template 214 to multiple slices of the online DTS image 204 to achieve a rough three-dimensional match.

The above technique is better than another possible method in which CT voxels are forward projected all the way to simulate projection images (rather than the above-described intermediate images) for reconstruction of the reference DTS images, thus saving computation time and resources. In addition, the above technique obviates the need to perform a back projection (like that required when a method of generating DRRs is used).

After the input DTS image 204 is obtained (and optionally processed to enhance a feature therein), and after the template image 220 has been obtained, the input image 204 is then compared with the template image 220 in the template matching process 206, like that described previously.

Figure 17:
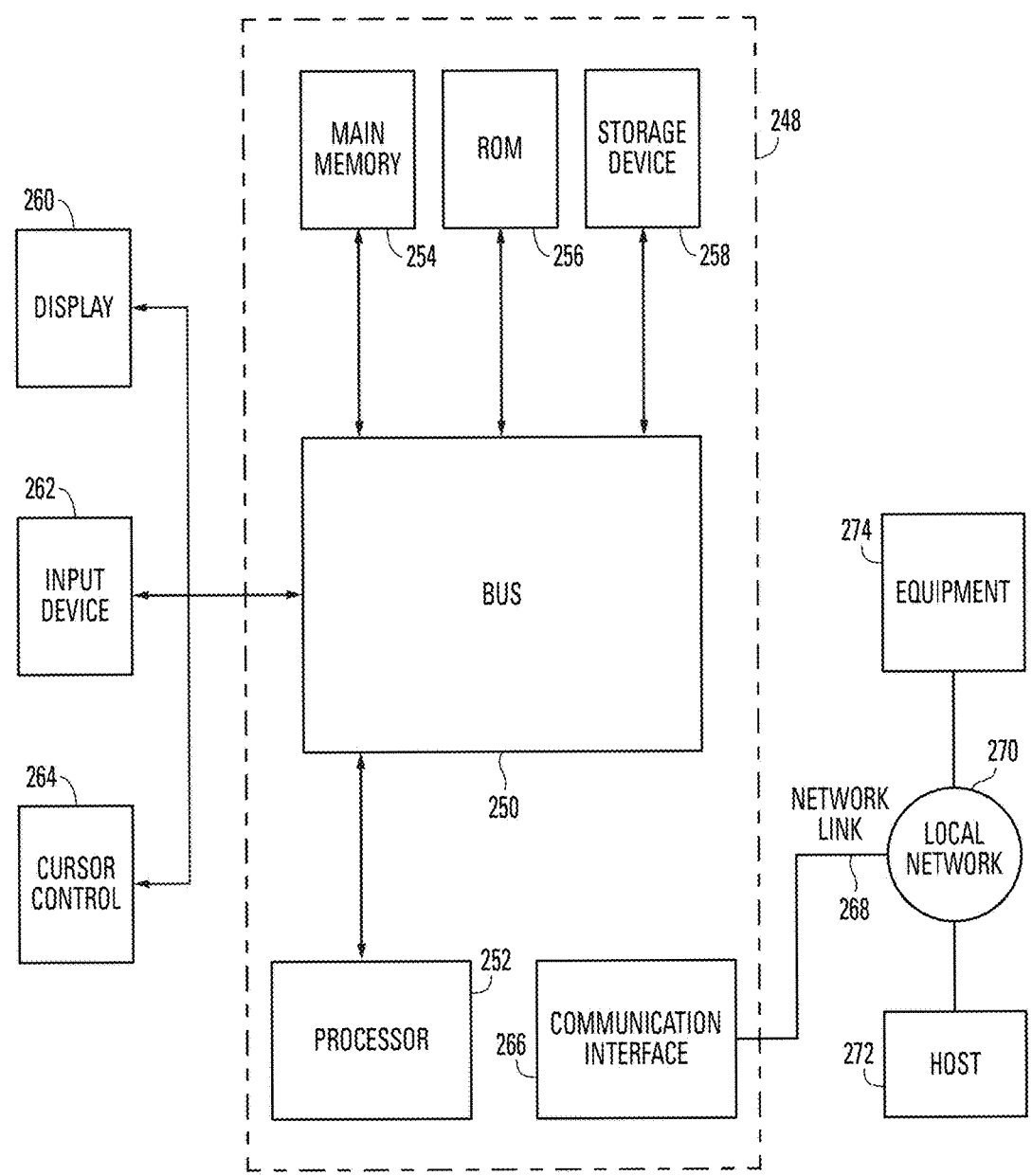
FIG. 17 is a block diagram illustrating a computer system with which embodiments of the present invention may be implemented.

FIG. 17 is a block diagram that illustrates an embodiment of a computer system 248 upon which an embodiment of the invention may be implemented. Computer system 248 includes a bus 250 or other communication mechanism for communicating information, and a processor 252 coupled with the bus 250 for processing information. The processor 252 may be an example of the processor 54 of FIG. 1, or another processor that is used to perform various functions described herein. In some cases, the computer system 248 may be used to implement the processor 54 (or other processors described herein). The computer system 248 also includes a main memory 254, such as a random access memory (RAM) or other dynamic storage device, coupled to the bus 250 for storing information and instructions to be executed by the processor 252. The main memory 254 also may be used for storing temporary variables or other intermediate information during execution of instructions to be executed by the processor 252. The computer system 248 further includes a read-only memory (ROM) 256 or other static storage device coupled to the bus 250 for storing static information and instructions for the processor 252. A data storage device 258, such as a magnetic disk or optical disk, is provided and coupled to the bus 250 for storing information and instructions.

The computer system 248 may be coupled via the bus 250 to a display 260, such as a cathode ray tube (CRT) or a flat panel, for displaying information to a user. An input device 262, including alphanumeric and other keys, is coupled to the bus 250 for communicating information and command selections to processor 252. Another type of user input device is cursor control 264, such as a mouse, a trackball, or cursor direction keys for communicating direction information and command selections to processor 252 and for controlling cursor movement on display 260. This input device typically has two degrees of freedom in two axes, a first axis (e.g., x) and a second axis (e.g., y), that allows the device to specify positions in a plane.

The computer system 248 may be used for performing various functions (e.g., calculation) in accordance with the embodiments described herein. According to one embodiment, such use is provided by computer system 248 in response to processor 252 executing one or more sequences of one or more instructions contained in the main memory 254. Such instructions may be read into the main memory 254 from another computer-readable medium, such as storage device 258. Execution of the sequences of instructions contained in the main memory 254 causes the processor 252 to perform the process steps described herein. One or more processors in a multi-processing arrangement may also be employed to execute the sequences of instructions contained in the main memory 254. In alternative embodiments, hardwired circuitry may be used in place of or in combination with software instructions to implement the invention. Thus, embodiments of the invention are not limited to any specific combination of hardware circuitry and software.

The computer system 248 also includes a communication interface 266 coupled to the bus 250. The communication interface 266 provides a two-way data communication coupling to a network link 268 that is connected to a local network 270. For example, the communication interface 266 may be an integrated services digital network (ISDN) card or a modem to provide a data communication connection to a corresponding type of telephone line. As another example, the communication interface 266 may be a local area network (LAN) card to provide a data communication connection to a compatible LAN. Wireless links may also be implemented. In any such implementation, the communication interface 266 sends and receives electrical, electromagnetic or optical signals that carry data streams representing various types of information.

The network link 268 typically provides data communication through one or more networks to other devices. For example, the network link 268 may provide a connection through local network 270 to a host computer 272 or to equipment 274 such as a radiation beam source or a switch operatively coupled to a radiation beam source. The data streams transported over the network link 268 can comprise electrical, electromagnetic or optical signals. The signals through the various networks and the signals on the network link 268 and through the communication interface 266, which carry data to and from the computer system 248, are exemplary forms of carrier waves transporting the information. The computer system 248 can send messages and receive data, including program code, through the network(s), the network link 268, and the communication interface 266.

The present invention has been described in particular detail with respect to possible embodiments. Those skilled in the art will appreciate that the invention may be practiced in other embodiments. The particular naming of the components, capitalization of terms, the attributes, data structures, or any other programming or structural aspect is not mandatory or significant, and the mechanisms that implement the invention or its features may have different names, formats, or protocols. The system may be implemented via a combination of hardware and software, as described, or entirely in hardware elements, or entirely in software elements. The particular division of functionality between the various system components described herein is merely exemplary and not mandatory; functions performed by a single system component may instead be performed by multiple components, and functions performed by multiple components may instead be performed by a single component.

In various embodiments, the present invention can be implemented as a system or a method for performing the above-described techniques, either singly or in any combination. In another embodiment, the present invention can be implemented as a computer program product comprising a computer-readable storage medium and computer program code, encoded on the medium, for causing a processor in a computing device or other electronic device to perform the above-described techniques.

As used herein, any reference to "one embodiment" or to "an embodiment" means that a particular feature, structure, or characteristic described in connection with the embodiments is included in at least one embodiment of the invention. The appearances of the phrase "in one embodiment" in various places in the specification are not necessarily all referring to the same embodiment.

Some portions of the above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is generally perceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared, transformed, and otherwise manipulated. It is convenient at times, principally for reasons of common usage, to refer to these signals as bits, values, elements, symbols, characters, terms, numbers, or the like. Furthermore, it is also convenient at times to refer to certain arrangements of steps requiring physical manipulations of physical quantities as modules or code devices, without loss of generality.

It should be borne in mind, however, that all of these and similar terms are to be associated with the appropriate physical quantities and are merely convenient labels applied to these quantities. Unless specifically stated otherwise as apparent from the following discussion, it is appreciated that, throughout the description, discussions utilizing terms such as "processing" or "computing" or "calculating" or "displaying" or "determining," or the like, refer to the action and processes of a computer system, or similar electronic computing module and/or device that manipulates and transforms data represented as physical (electronic) quantities within the computer system memories or registers or other such information storage, transmission, or display devices.

Certain aspects of the present invention include process steps and instructions described herein in the form of an algorithm. It should be noted that the process steps and instructions of the present invention can be embodied in software, firmware and/or hardware, and, when embodied in software, can be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but not limited to, any type of disk, including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers and/or other electronic devices referred to in the specification may include a single processor or may be architectures employing multiple processor designs for increased computing capability.

The algorithms and displays presented herein are not inherently related to any particular computer, virtualized system, or other apparatus. Various general-purpose systems may also be used with programs in accordance with the teachings herein, or it may prove convenient to construct more specialized apparatus to perform the required method steps. The required structure for a variety of these systems will be apparent from the description provided herein. In addition, the present invention is not described with reference to any particular programming language. It will be appreciated that a variety of programming languages may be used to implement the teachings of the present invention as described herein, and any references above to specific languages are provided for disclosure of enablement and best mode of the present invention.

In various embodiments, the present invention can be implemented as software, hardware, and/or other elements for controlling a computer system, computing device, or other electronic device, or any combination or plurality thereof. Such an electronic device can include, for example, a processor, an input device (such as a keyboard, mouse, touchpad, trackpad, joystick, trackball, microphone, and/or any combination thereof), an output device (such as a screen, speaker, and/or the like), memory, long-term storage (such as magnetic storage, optical storage, and/or the like), and/or network connectivity, according to techniques that are well known in the art. Such an electronic device may be portable or non-portable. Examples of electronic devices that may be used for implementing the invention include a mobile phone, personal digital assistant, smartphone, kiosk, desktop computer, laptop computer, consumer electronic device, television, set-top box, or the like. An electronic device for implementing the present invention may use an operating system such as, for example, iOS available from Apple Inc. of Cupertino, Calif., Android available from Google Inc. of Mountain View, Calif., Microsoft Windows 7 available from Microsoft Corporation of Redmond, Wash., webOS available from Palm, Inc. of Sunnyvale, Calif., or any other operating system that is adapted for use on the device. In some embodiments, the electronic device for implementing the present invention includes functionality for communication over one or more networks, including for example a cellular telephone network, wireless network, and/or computer network such as the Internet.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The terms "a" or "an," as used herein, are defined as one or more than one. The term "plurality," as used herein, is defined as two or more than two. The term "another," as used herein, is defined as at least a second or more.

An ordinary artisan should require no additional explanation in developing the methods and systems described herein but may, nevertheless, find some possibly helpful guidance in the preparation of these methods and systems by examining standard reference works in the relevant art.

While the invention has been described with respect to a limited number of embodiments, those skilled in the art, having benefit of the above description, will appreciate that other embodiments may be devised which do not depart from the scope of the present invention as described herein. It should be noted that the language used in the specification has been principally selected for readability and instructional purposes, and may not have been selected to delineate or circumscribe the inventive subject matter. The terms used should not be construed to limit the invention to the specific embodiments disclosed in the specification and the claims but should be construed to include all methods and systems that operate under the claims set forth herein below. Accordingly, the invention is not limited by the disclosure, but instead its scope is to be determined entirely by the following claims.

What is claimed and desired to be secured by Letters Patent of the United States is:

1. A method to optimize a treatment delivery that includes tracking of a target, comprising:
   simulating, using a processor, a treatment time image from treatment planning images and data to obtain a simulated treatment time image, wherein the processor comprises an input configured to receive the treatment planning images and the data, and is configured to simulate the treatment time image based at least in part on the treatment planning images and the data;
   generating, using the processor, a template from the planning images and data;

template matching, using the processor, between the template and the simulated treatment time image to determine a value of a trackability measure as part of treatment planning, the trackability measure indicating a trackability of the target and being a function of imaging angle; and determining, using the processor, a treatment plan based on the value of the trackability measure;

wherein the treatment plan determined based on the value of the trackability measure, is executable by a treatment machine to cause the treatment machine to deliver less or no dose from a treatment delivery angle for which one of a plurality of values of the trackability measure is lower compared to another one of the plurality of values of the trackability measure for another treatment delivery angle.

2. The method of claim 1, further comprising optimizing a selection of a template generation and imaging modality, wherein the optimizing comprises:

for each of a plurality of imaging angles, searching through template generation methods and imaging modalities to maximize the trackability measure.

3. The method of claim 2, where the imaging angles comprise angles from 0 degree to 360 degrees by discrete increments.

4. The method of claim 2, wherein the optimizing step comprises looping through template generation methods and imaging modalities for the imaging angles.

5. The method of claim 1, wherein the trackability measure comprises a peak-to-side lobe ratio.

6. The method of claim 1, wherein the treatment time image comprises digital reconstructed radiograph (DRR).

7. The method of claim 1, wherein the treatment time image comprises dual energy (DE) digital reconstructed radiograph (DRR).

8. The method of claim 1, wherein the treatment time image comprises megavoltage (MV) digital reconstructed radiograph (DRR).

9. The method of claim 1, wherein the treatment time image comprises kilovoltage (KV) digital reconstructed radiograph (DRR).

10. The method of claim 1, wherein the treatment time image comprises digital tomosynthesis (DTS) image.

11. The method of claim 1, wherein the treatment time image comprises megavoltage/kilovoltage (MV/KV) digital reconstructed radiograph (DRR).

12. A method to predict trackability of a target as part of treatment planning, comprising:

simulating, using a processor, a treatment time image from a plan computed tomography (CT) image, wherein the processor comprises an input configured to receive the plan CT image, and is configured to simulate the treatment time image based at least in part on the plan CT image;

generating, using the processor, a template from planning data;

template matching, using the processor, between the template and the simulated treatment time image to determine a value of a trackability measure indicating a target tracking performance; and generating an electronic file representing a treatment plan, the electronic file being stored in a non-transitory medium and being executable by a processing unit of a treatment system, wherein the generated electronic file representing the treatment plan prescribes a tracking scheme that is based on the value of the trackability measure determined via the template matching between the template and the simulated treatment time image;

wherein the treatment plan is executable by the processing unit of the treatment system to cause the treatment system to deliver less or no dose from a treatment delivery angle for which one of a plurality of values of the trackability measure is lower compared to another one of the plurality of values of the trackability measure for another treatment delivery angle.

13. The method of claim 12, wherein the treatment time image comprises digital reconstructed radiograph (DRR).

14. The method of claim 12, wherein the treatment time image comprises dual energy (DE) digital reconstructed radiograph (DRR).

15. The method of claim 12, wherein the treatment time image comprises megavoltage (MV) digital reconstructed radiograph (DRR).

16. The method of claim 12, wherein the treatment time image comprises kilovoltage (KV) digital reconstructed radiograph (DRR).

17. The method of claim 12, wherein the treatment time image comprises digital tomosynthesis (DTS) image.

18. The method of claim 12, wherein the treatment time image comprises megavoltage/kilovoltage (MV/KV) digital reconstructed radiograph (DRR).

19. The method of claim 12, further comprising selecting an imaging modality for use in a treatment procedure based on the target tracking performance.

20. The method of claim 12, further comprising selecting a template generation for use in a treatment procedure based on the target tracking performance.

21. A program product comprising a processor readable storage medium structured to store instructions executable by a processor, the instructions, when executed cause the processor to perform a method that comprises:

simulating, using the processor, a treatment time image from treatment planning images and data, wherein the processor comprises an input configured to receive the treatment planning images and the data, and is configured to simulate the treatment time image based at least in part on the treatment planning images and the data;

generating, using the processor, a template from the planning images and data;

template matching, using the processor, between the template and the simulated treatment time image to determine a value of a trackability measure as part of treatment planning, the trackability measure indicating a trackability of a target and being a function of imaging angle; and determining a treatment plan based on the value of the trackability measure;

wherein the treatment plan determined based on the value of the trackability measure, is executable by a treatment machine to cause the treatment machine to deliver less or no dose from a treatment delivery angle for which one of a plurality of values of the trackability measure is lower compared to another one of the plurality of values of the trackability measure for another treatment delivery angle.

22. The program product of claim 21, wherein the method further comprises selecting, using the processor, an imaging modality for use in a treatment procedure based on an optimization of the trackability measure.

23. The program product of claim 21, wherein the method further comprises selecting, using the processor, a template generation for use in a treatment procedure based on an optimization of the trackability measure.

* * * * *